(12) United States Patent
Sedlacek et al.

(10) Patent No.: US 6,384,202 B1
(45) Date of Patent: May 7, 2002

(54) CELL-SPECIFIC ACTIVE COMPOUNDS REGULATED BY THE CELL CYCLE

(75) Inventors: Hans-Harald Sedlacek; Rolf Müller, both of Marburg (DE)

(73) Assignee: Hoechst Aktiengesellschaft, Frankfurt am Main (DE)

(*) Notice: Subject to any disclaimer, the term of this patent is extended or adjusted under 35 U.S.C. 154(b) by 0 days.

This patent is subject to a terminal disclaimer.

(21) Appl. No.: 08/793,109

(22) PCT Filed: Aug. 25, 1995

(86) PCT No.: PCT/EP95/03371

§ 371 Date: Apr. 25, 1997

§ 102(e) Date: Apr. 25, 1997

(87) PCT Pub. No.: WO96/06941

PCT Pub. Date: Mar. 7, 1996

(30) Foreign Application Priority Data

Aug. 26, 1994 (GB) .............................................. 9417366
Mar. 29, 1995 (GB) .............................................. 9506466
Jul. 12, 1995 (DE) .......................................... 195 24 720

(51) Int. Cl.[7] ........................ A01N 63/00; A61K 48/00; C07H 21/02; C12N 15/63
(52) U.S. Cl. .................... 536/23.1; 424/93.1; 424/93.2; 424/93.6; 435/320.1; 536/23.5; 536/24.1
(58) Field of Search .............................. 536/23.5, 24.1, 536/23.1; 514/44; 435/320.1; 424/93.1, 93.2, 93.6

(56) References Cited

U.S. PATENT DOCUMENTS

| | | | |
|---|---|---|---|
| 5,830,880 A | 11/1998 | Sedlacek et al. | ............... 514/44 |
| 5,854,019 A | 12/1998 | Sedlacek et al. | ............ 435/69.1 |
| 5,885,833 A | 3/1999 | Muller et al. | ................ 435/372 |
| 5,916,803 A | 6/1999 | Sedlacek et al. | ......... 435/320.1 |

OTHER PUBLICATIONS

Friedmann, T. Overcoming the obstacles to gene therapy. Sci. Am., Jun. 1997, pp. 96–101.*

Orkin and Motulsky, Report and recommendations of the panel to assess the NIH investment in research on gene therapy, Dec. 1995.*

Verma et al. Gene therapy—promises, problems and prospects. Nature 389:239–242, Sep. 1997.*

* cited by examiner

*Primary Examiner*—Deborah J. R. Clark
*Assistant Examiner*—Anne-Marie Baker
(74) *Attorney, Agent, or Firm*—Heller Ehrman White and McAuliffe

(57) ABSTRACT

A DNA sequence is described for the gene therapy of diseases associated with the immune system. In its essential elements, the DNA sequence is composed of an activator sequence, a promoter module and a gene for the active substance. The activator sequence is activated in a cell-specific or virus-specific manner and this activation is regulated by the promoter module in a cell cycle-specific manner. The choice of activator sequence and active substance depends on the indication area. The DNA sequence is inserted into a viral or non-viral vector which is supplemented by a ligand having affinity for the target cell. Depending on the choice of activator sequence and active substance, the following can be treated by administering the DNA sequence: defective formation of blood cells; autoimmune diseases and allergies and, in addition, rejection reactions against transplanted organs; chronic arthritis; viral and parasitic infections and, in addition, prophylaxis of viral, bacterial and parasitic infections; and leukemias.

23 Claims, 15 Drawing Sheets

Figure 1:
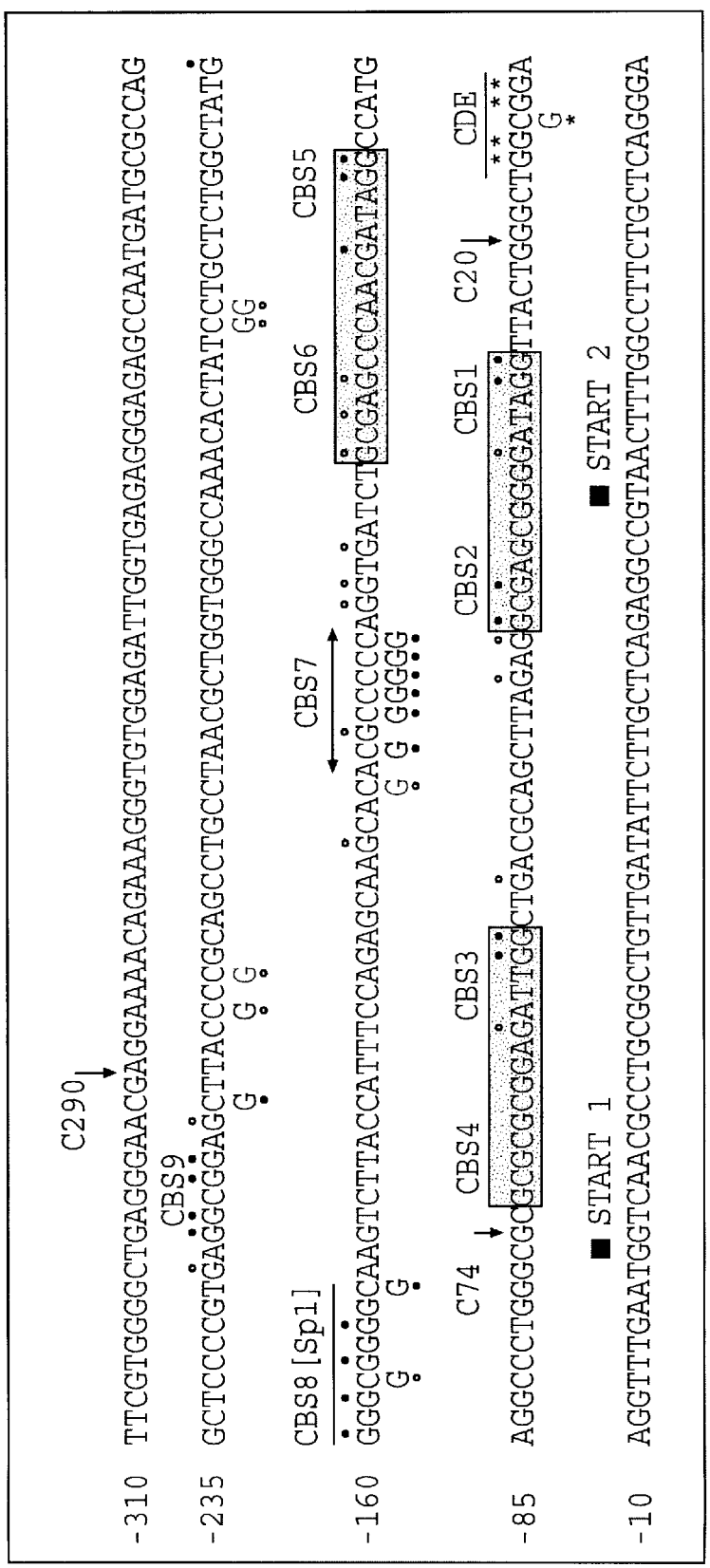

```
-500  ATGGCTTCCC ATATCCCAGA GAGTAAGAAC CAGAGAGAGA GAGAGAAAGA GAGAGAGTTT
-440  GGGTCTTTCT CCTCTGTGCC TGCTCTCTCC AGAGAAACTG GAGGGGTAGC AGTTAGCATT
-380  CCCCGCTGG TTCCACCAAG CACAGTCAAG GTCTCTAGGA CATGGCCACC CCTCACCTGT
-320  GGAAGCGGTC CTGCTGGGGT GGGTGGGTGT TAGTTGGTTC TGGTTTGGGT CAGAGACACC
                                     NF1
-260  CAGTGGCCCA GGTGGCGTG GGGCCAGGGC GCAGACGAGA AGGGGCACGA GGGCTCCGCT
-200  CCGAGGACCC AGCGGCAAGC ACCGGTCCCG GGCGCGCCCA AGCCCACCCA CTCGGCGTGC
                                                         SP1    SP1
-140  CACGGGCGGCA TTATTCCCTA TAAGGATCTG AACGATCCGG GGGCGGGCCC GCCCCGTTAC
                 SP1                                           C/EBP
 -80  CCCTTGCCCC CGGCCCCGCC CCCTTTTTGG AGGGCCGATG AGTAATGCG GCTCTGCCAT
                 SP1       ↓ START
 -20  TGGTCTGAGG GGGCGGGCCC CAACAGCCCG AGGCGGGGTC CCCGGGGCC CAGCGCTATA
 +42  TCACTCGGCC GCCCAGGCAG CGGGGCAGAG CGGGGCAGCG GCAGGCGGCG GGGCGTCAGA
```

FIG. 9

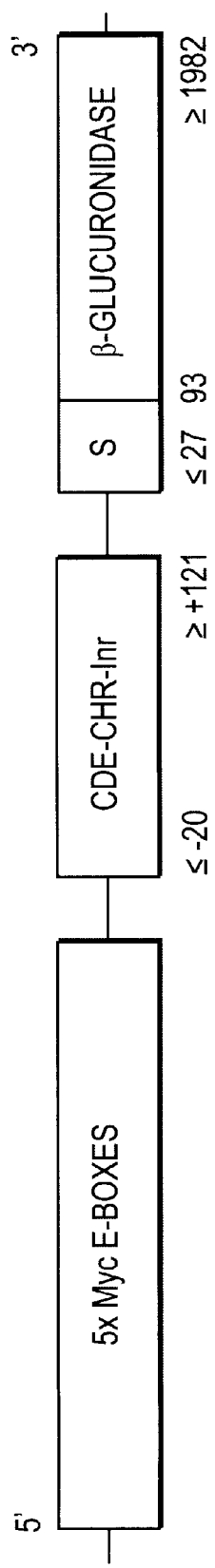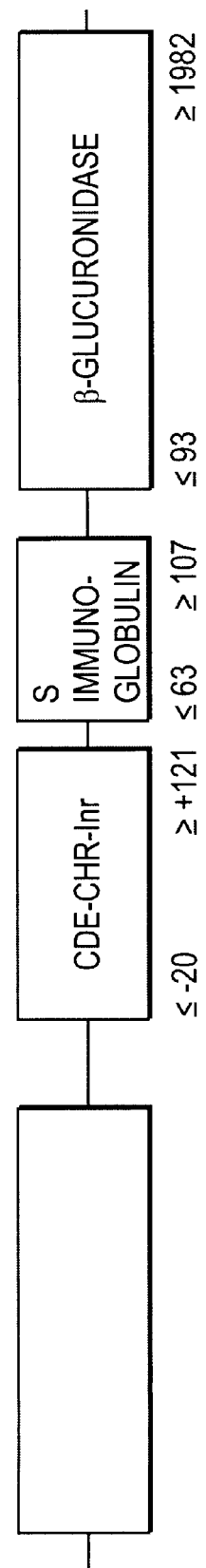

CELL-SPECIFIC ACTIVE COMPOUNDS REGULATED BY THE CELL CYCLE

TECHNICAL FIELD

A DNA sequence is described for the gene therapy of diseases associated with the immune system.

In its essential elements, the DNA sequence is composed of an activator sequence, a promoter module and a gene for the active substance.

The activator sequence is activated in a cell-specific or virus-specific manner and this activation is regulated by the promoter module in a cell cycle-specific manner. The choice of activator sequence and active substance depends on the indication area. The DNA sequence is inserted into a viral or non-viral vector, which vector is supplemented with a ligand having affinity for the target cell.

Depending on the choice of activator sequence and active substance, the following can be treated by administering the DNA sequence:

defective formation of blood cells autoimmune diseases and allergies and, in addition, rejection reactions against transplanted organs chronic arthritis viral and parasitic infections and, in addition, prophylaxis of viral, bacterial and parasitic infections, and leukemias.

A defective immune system causes an extremely wide variety of diseases. These include, for example, allergies, autoimmune diseases and chronic inflammations, in particular chronic arthritis, due to erroneous functioning of the immune system rejection of transplanted organs due to the immune system not being adequately inhibited poor vaccination results and chronic infections, for example by viruses, as a consequence of immune deficiency leukemias and lymphomas as tumorous degeneration of the immune system.

As is well known, the current therapeutic possibilities for diseases of this nature are inadequate. This will be illustrated using a few examples.

1) Therapy with Cytokines

By now, a substantial number of cytokines and growth factors have become known which are involved in the differentiation, multiplication, maturation and functioning of cells.

For example, the hematopoietic system is controlled by a hierarchy of different cytokines, which ensure, by means of their differing functions, the multiplication of the individual differentiation stages and, over and above the individual differentiation stages, the ongoing formation of mature blood cells such as erythrocytes, thrombocytes, granulocytes, macrophages and lymphocytes (Dexter et al., Haematopoietic Growth Factors, Gardiner Well Communication, Macclesfield (1993)).

In addition, it is known that cytokines and growth factors play an important role in the cooperation of cells with each other (Pusztal et al., J. Pathol. 169, 191 (1993), Cross et al., Cell 64, 271 (1991)).

Thus, in immune resistance, for example, the collaboration between antigen-presenting cells, T lymphocytes and B lymphocytes is controlled by different cytokines with the sequence and concentration of the cytokines being crucial for the nature and strength of the immune reaction (Aulitzky et al., Drugs 48, 667 (1994), Sedlacek et al., Immune Reactions, Springer Verlag (1995)). In addition, resistance to infectious agents, such as viruses, is both influenced and supported by cytokines such as interferons (Edgington, Biotechnol. 11, 465 (1993)).

Knowledge of these relationships has already led to the development of cytokines for the therapy of human diseases, for example of erythropoietin for curing anemia G-CSF for curing neutropenia GM-CSF for curing leukopenia IL-2 for immune resistance to selected tumors IFNα for the therapy of chronic viral hepatitis IFNβ for the therapy of multiple sclerosis Further cytokines are currently being tested (Aulitzky et al., Drugs 48, 667 (1994)). These include, for example thrombopoietin for curing thrombocytopenia (Metcalf, Nature 369, 519 (1994))

IL-3 for tumor therapy (de Vries et al., Stem Cells 11, 72 (1993) and for providing support in curing cytopenic conditions of the hematopoietic system (Freudl, Int. J. Immunopharm. 14, 421 (1992))

IL-4 for tumor therapy (Manate et al., Blood 83, 1731 (1994))

IL-6 for curing cytopenic conditions of the hematopoietic system (Brack et al., Int. J. Clin. Lab. Res. 22, 143 (1992))

IL-10 for immunosuppression (Benjamin et al., Leuk. Lymph. 12, 205 (1994))

IL-11 for curing thrombocytopenia (Kobayashi et al., Blood 4, 889 (1993)) IL-12 for tumor therapy (Tahara et al., Cancer Res. 54, 182 (1994))

TNFα for tumor therapy (Porter, Tibitech 9, 158 (1991)).

A common feature of therapy with all cytokines is the disadvantage that they usually have to be administered parenterally every day over a relatively long period of time and, furthermore, that, for their greatest possible efficacy, several cytokines either have to be injected one after the other in the necessary hierarchical sequence or corresponding cytokines have to be present in adequate concentration in the body.

That which is crucial for the effect is the concentration of the particular cytokines at the site of the cell which is to be stimulated. For the sake of simplicity, the cytokines are injected daily either subcutaneously or i.m. While this mode of administration guarantees a delayed systemic distribution, which is what is sought-after, relatively high quantities have to be administered in order to ensure an adequate local concentration at the site of the desired effect. The increased dose which is consequently required constitutes, due to the high level of expenditure involved in producing cytokines, a substantial cost factor which considerably restricts the use of cytokines.

Over and above this, some cytokines give rise, in the therapeutic dose range, to substantial side effects. IL-1 (Smith et al., New Engl. J. Med. 328, 756 (1993)), IL-3 (Kurzrock et al., J. Clin. Oncol. 9, 1241 (1991)) and Il-2 (Siegel et al., J. Clin. Oncol. 9, 694 (1991)) are examples of such cytokines.

Consequently, there is a substantial requirement for novel methods for making cytokines or combinations of cytokines available over a relatively long period of time, and in adequate concentration, at their site of action.

2) Chronic Arthritis

Despite improved antiinflammatory and immunosuppressive medicaments, chronic arthritis is a disease for which only inadequate therapeutic measures are available and which substantially reduces the quality of life and can even shorten life expectancy (Pincus et al., Bull. Rheum. Dis. 41, 1 (1992)). Because of its frequency (approx. 10% of the population of the western world suffers from arthritis) arthritis constitutes a substantial cost factor for national economies.

In view of the fact that medicinal therapy is inadequate, surgical removal of the synovial membranes of the joint capsule (synovectomy) or surgical replacement of the joint is the last possible form of therapy for many patients.

In view of these medicinal and economic problems, chronic arthritis represents a challenge for pharmaceutical research.

However, it can already be predicted today that, irrespective of their nature, medicaments which are administered orally or parenterally will have difficulty in reaching the region of joint inflammation in adequate concentration since they have to diffuse through the synovial capillaries and then passively through the synovial membrane into the joint cavity and from there into the cells lining the joint (Evans et al., Gene Therapeutics, J. Wolff, Editor, page 320, Birkhäuser, Boston 1994).

This diffusion is additionally made more difficult by the fact that the vascularization of the synovial membrane is significantly reduced in rheumatoid arthritis, for example (Stevens et al., Arthritis Rheum. 34, 1508 (1991)). While intraarticular injection of medicaments circumvents the problem of diffusion, the dwell time of the medicament in the joint is so short, owing to the high reabsorption rate, that repeated intraarticular injections over a relatively long period of time are required. These injections are in turn associated with the considerable risk of a joint infection. In addition, they can give rise to substantial side effects on account of the high local concentration of the medicament which is required.

In order to remedy these problems, the systemic or local, intraarticular administration of vectors or of in-vitro transduced synovial cells has been proposed for the therapy of chronic arthritis (Bandara et al., DNA Cell Biol. 11, 227 (1992), BBA 1134, 309 (1992) Evans et al., Transplant. Proc. 24, 2966 (1992)).

The principle of this gone therapy is that of using cells which are transduced in vivo in the joint cavity, or of using the injection into the joint cavity of synovial cells which have been transduced in vitro, to achieve high concentrations of antiarthritic substances, for example (Evans et al., J. Rheumatol. 21, 779 (1994))

antiinflammatory cytokines
(e.g. IL-1 receptor antagonist, IL-4 or IL-10)
cytokine inhibitors
(e.g. soluble receptors for IL-1, TNFα, IL-8, TGFα, or for other cytokines and interleukins which amplify inflammation)
enzyme inhibitors
(e.g. TIMP, LIMP, IMP, PAI-1, PAI-2 and others)
anti-adhesion molecules
(e.g. soluble CD-18, ICAM-1 and soluble CD44)
antagonists of oxygen radicals
(e.g. superoxide dismutase)
or of growth factors for cartilage cells
(e.g. TGFβ or IGF-1)

Animal experiments carried out in the rabbit have demonstrated grounds for IL-1-RA which is expressed following intraarticular injection of the corresponding gene having activity (Bandara et al., PNAS 90, 10764 (1993), Hung et al., Gene Therapy 1, 64 (1994)).

In principle, however, these methods for gene therapy which have hitherto been proposed suffer from considerable disadvantages When synovial cells are transduced in vitro, they have to be removed from the joint cavity. This in itself puts a strain on the patient and carries the risk of a Joint infection. In the second place, synovial cells can only be isolated with great difficulty and in small numbers. Consequently, the synovial cells have to be replicated in vitro so that they can be transduced in sufficient number. However, it is known that it is only the fibroblast-like synovial cells (type B), and not the macrophage-like type A, which can be replicated under standard conditions of cell culture (Evans et al., Gene Therapeutics, page 320, J. A. Wolff, Editor, Birkäuser Boston (1994)). Consequently, the injection of synovial cells which are transduced in vitro suffers from substantial problems and will usually not be technically possible to achieve or only possible to achieve with considerable effort.

In the case of the systemic or intraarticular injection of vectors, which is under discussion, for transducing cells in vivo (Evans et al., Gene Therapeutics, page 320, J. A. Wolff, Editor, Birkäuser Boston (1994)), there is no regulatory mechanism which enables the genes which are transferred by way of the vector only to be expressed in those cells which are involved in chronic arthritis and then only if the cells are activated in the sense of an inflammation. In the absence of such a regulatory mechanism, cells which are distributed over the whole of the body are transduced, following systemic administration of the vector, to produce the particular antiarthritic substance, which would either lead to a systemic effect on the immune reaction or, in relation to the arthritic inflammatory process, be synonymous with the repeated systemic administration of antiarthritic active compounds, which administration is, per se, already regarded as being ineffective or insufficiently effective.

Following local administration, it would be possible, depending on the vector employed, to transduce in vivo either proliferating cells in the main (using an RTV vector) or resting cells as well (using other viral or non-viral vectors) to produce the antiarthritic substance. Since a large proportion of such substances have an antiinflammatory effect, the immune and inflammatory reactions in the joints would be inhibited independently of whether the chronic arthritis was in a resting phase or in an acute disease episode. Favored by the local inhibition of the immune reaction, and brought about by the causal factors of chronic arthritis, there would be the risk of an intensified pathological immune and inflammatory reaction once the activity of the antiarthritic substances had subsided, but no extensive alleviation or curing of the arthritis.

Consequently, there is a pressing requirement for novel therapeutic processes or active compounds
which can be administered locally or systemically to a patient depending on the number and severity of the chronically inflamed joints,
whose effect is principally, if not exclusively, restricted to activated and proliferating synovial cells or inflammatory cells, whose effects primarily consist of the relatively long-term prophylaxis and therapy of the acute inflammatory episode.

3) Leukemias and Lymhomas

Patients who have tumors of the hematopoietic system and who suffer a relapse after temporarily successful chemotherapy have a relatively poor prognosis (Hiddemann et al., Blood Rev. 8, 225 (1994)). As a consequence, various intensive treatment strategies have been developed for prolonging survival time.

These strategies include different combinations of cytostatic agents (The Medica Letter 31, 49 (1989)) and also bone marrow transplantation (De Magalhaos-Silverman et al., Cell Transplant. 2, 75 (1993)). However, the efficacy of both these approaches to therapy is only limited (Sloane et al., Histophathol. 22 201 (1993)). Consequently, there is still a substantial medical requirement for novel, effective therapeutic agents for tumors of the hematopoietic system.

Tumor cells of the hematopoietic system exhibit pronounced molecular biological changes which depend on the type of tumor (Reviews in Lotter et al., Cancer Surveys 16, 157 (1993) and Yunis et al., Crit. Rev. Onc. 4, 161 (1993)). The following are examples of those which are particularly pronounced in this context Burkitt's lymphomas (BL)—Deregulation of c-myc together with excessive production of c-myc mRNA and c-myc protein (McKeithan, Seminars in Oncol. 17, 30 (1990))
Overexpression of bcl-2 (Tsujimoto et al., PNAS 86, 1958 (1989))
B cell leukemias and lymphomas (BCL)
Overexpression of bcl-2 (in 85% of patients suffering from follicular lymphoma and 25% of patients suffering from diffuse lymphoma) (Yunis et al., New Engl. J. Med. 316, 79 (1987))
Overexpression of bcl-1 in patients suffering from centrocytic lymphoma (Seto et al., Oncogene 7, 1401 (1992))
Overexpression of IL-6 (Lewis et al., Nature 317, 544 (1985))
Overexpression of IL-10 (Levine, Blood 80, 8 (1992))
acute B cell leukemia (aBCL)
Expression of the fusion protein E2A-PBX-1 (Yunis et al., Crit. Rev. Onco. 4, 161 (1993))
T cell lymphomas (TCL)
Overexpression of c-myc (Cotter, Cancer Surveys 16, 157 (1993))
Overexpression of HOX11 (syn. TCL3) (Hatano et al., Science 253, 79 (1991))
chronic myeloid leukemia (CML)
Expression of the fusion protein BCR-Abl (Daley et al., PNAS 88, 11335 (1991))
acute lymphatic leukemia (ALL)
Overexpression of IL-3 (Mecker et al., Blood 76, 285 (1990))
acute myeloid leukemia (AML)
Expression of the fusion protein PML/RARA (Alcalay et al., PNAS 89, 4840 (1992)) Pandolfi et al., EMBO J. 11, 1397 (1992))

However, it has so far not been possible to use these molecular biological changes for clinical therapeutic methods.

4) General Description of the Invention

The present invention now relates to an active compound (i.e. a pharmaceutical) which can be administered to patients both locally and systemically and which brings about a cell-specific, cell-cycle regulated formation of active substances for the therapy of diseases of the immune system.

An essential constituent of the active compound is a DNA construct of the following composition

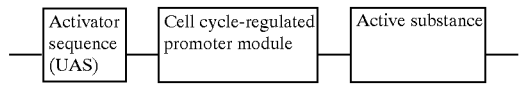

(In the whole of the text for this application, DNA is used as a common term both for a complementary (cDNA) and a genomic DNA sequence).

4.1. Description of the promoter module

The central element of the novel active compound is a cell cycle-regulated promoter module.

A cell cycle-regulated promoter module is to be understood, for example, to be the nucleotide sequence -CDE-CHR-Inr- (see below). The essential function of the promoter module moiety is that of inhibiting the function of the activator sequence in the G0/G1 phase of the cell cycle and that of ensuring cell cycle-specific expression in the S/G2 phase and consequently in proliferating cells.

Figure 2:
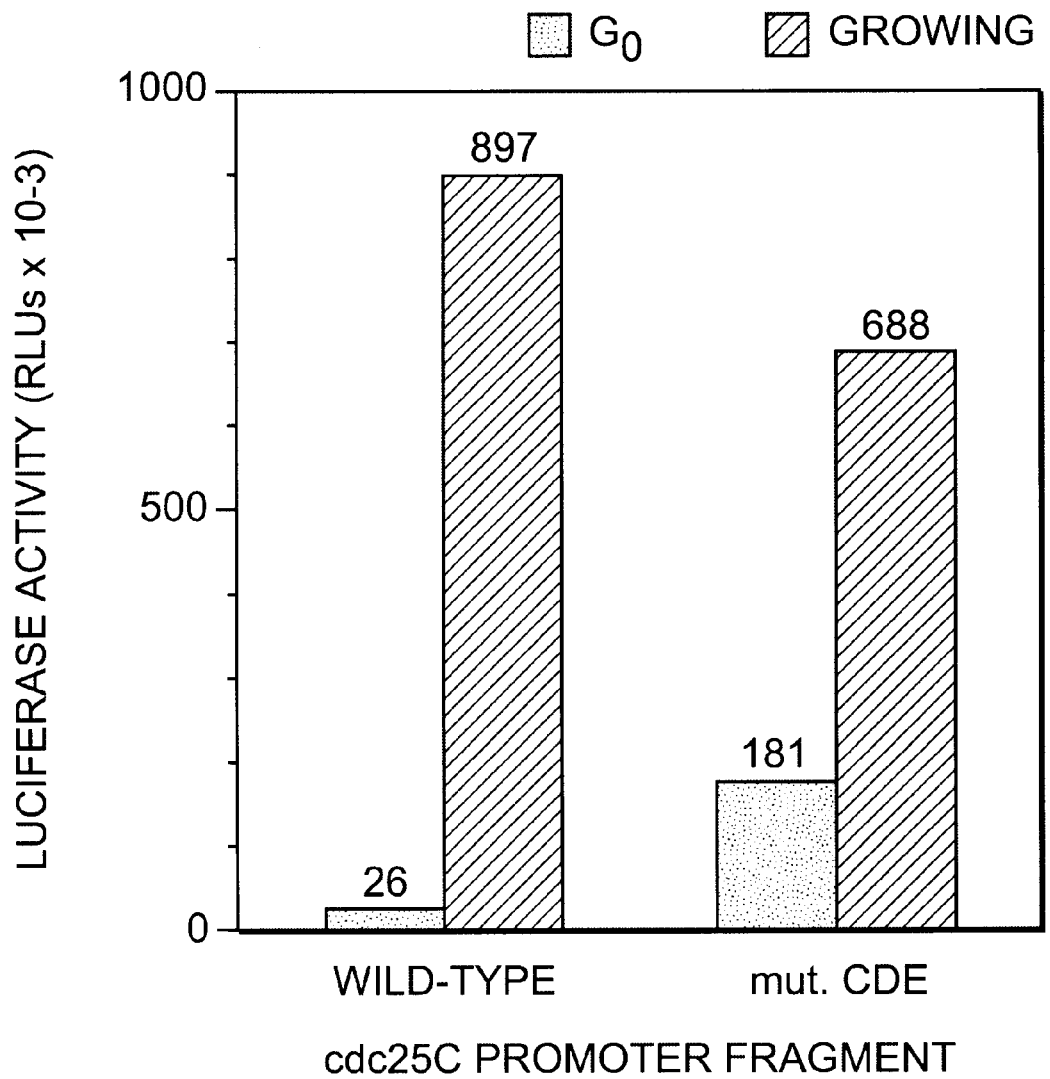
Figure 3:
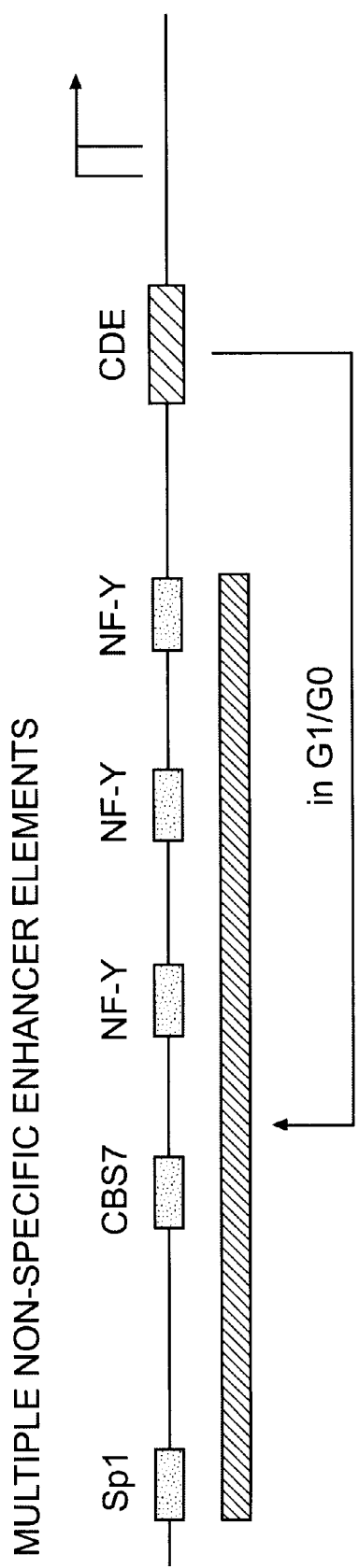

The promoter module CDE-CER-Inr was discovered in the context of a detailed investigation of the G2-specific expression of the human cdc25C promoter. The starting point was finding a repressor element (cell cycle dependent element; CDR) which is responsible for switching off the promoter in the G1 phase of the cell cycle (Lucibello et al., EMBO U. 14, 132 (1995)). Using genomic dimethyl sulfate (DMS) footprinting and functional analyses (FIGS. 1 and 2), it was possible to demonstrate that the CDE binds a repressor (CDE-binding factor; CDF) in a G1-specific manner and in this way gives rise to conscription inhibition in non-proliferating (G0) cells. The CDE, which is located in the region of the basal promoter, depends, in its repressing function, on an upstream activating sequence (UAS). This led to the conclusion that the CDE-binding factor inhibits the transcription-activating effect of 5'-bound activator proteins in a cell cycle-dependent manner, i.e. in both non-proliferating cells and in the G1 phase of the cell cycle (FIG. 3).

Figure 4:
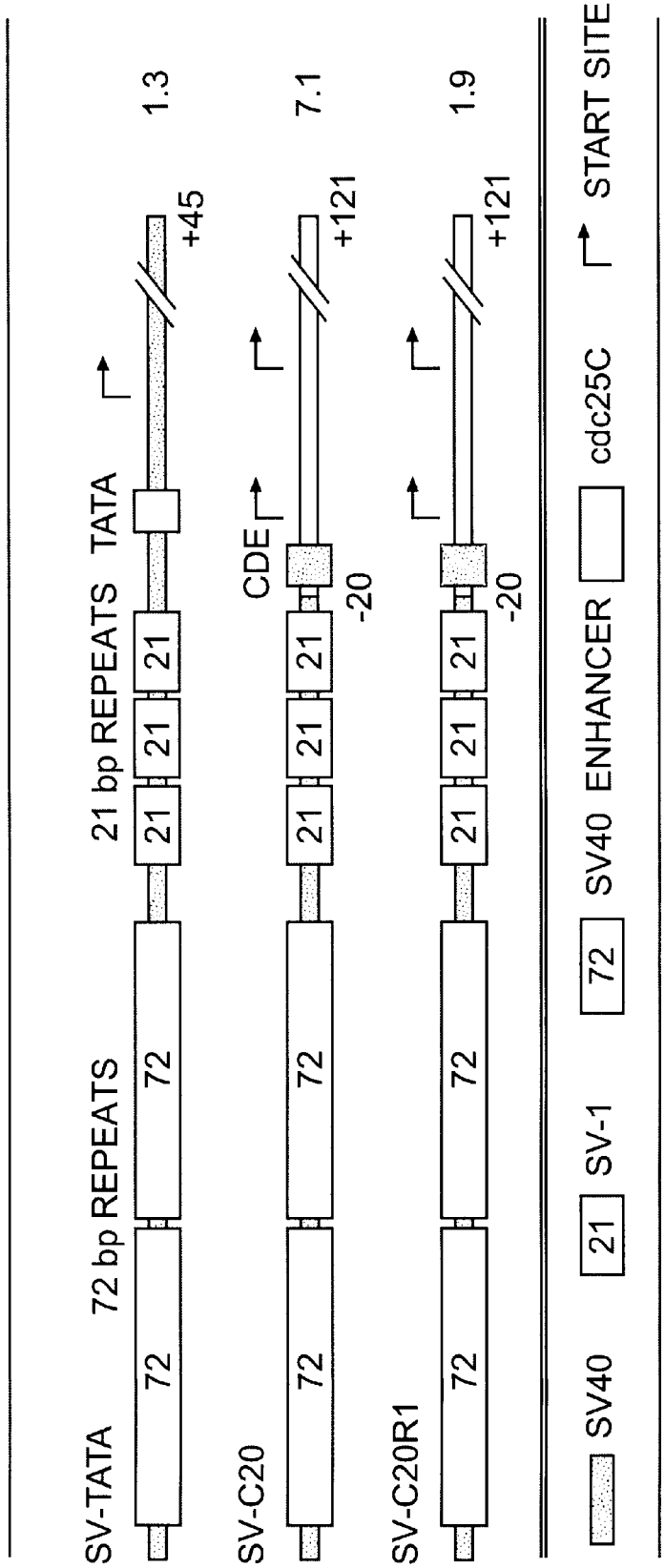

It was possible to confirm this conclusion by a further experiment: fusion of the viral, non-cell cycle-regulated early Sv40 enhancer with a cdc25 minimum promoter (consisting of CDE and the start sites situated 3') led to clear cell cycle-regulation of the chimeric promoter (FIG. 4). Subsequent investigations on the cdc25C enhancer have demonstrated that the transcription factors which are regulated by CDF in a cell cycle-dependent manner are NF-Y (CBF) (Dorn et al., Cell 50, 863 (1987), van Hijisduijnen et al., EMBO J. 9, 3119 (1990), Country et al., J. Biol. Chem. 270, 468 (1995)), Sp1 (Kadonaga et al., TIBS 11, 10 (1986) and a transcription factor (CIF) which is possibly novel and which binds to CBS7. Another interesting finding made in this study was the observation that NF-Y within the cdc25C enhancer only activates transcription efficiently in cooperation with at least one further NF-Y complex or with CIF. Both NF-Y and Sp1 belong to the glutamine-rich activator class, which provides important pointers to the mechanism of repression (e.g. interaction or interference with particular basal transcription factors or TAFs).

Figure 5:
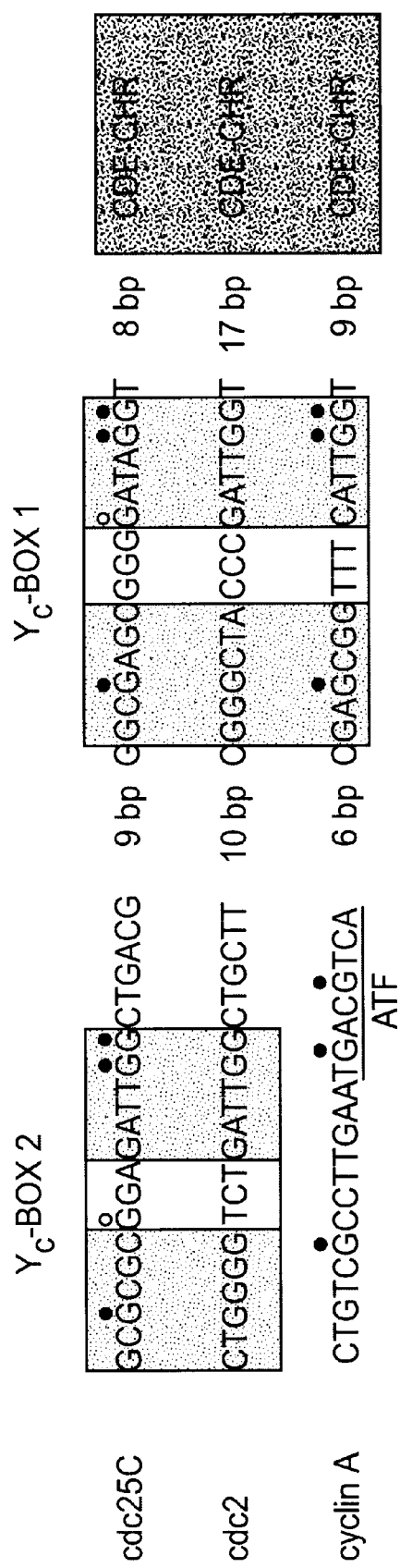

A comparison of the promoter sequences of cdc25C, cyclin A and cdc2 demonstrated homologies in several regions in several regions (FIG. 5, SEQ ID NOS 2–7). It is not only the CDE which is conserved in all three promoters (the divergencies which are present are not functionally relevant) but also the neighboring $Y_c$ boxes. As expected, all these regions exhibited protein binding in vivo, with this protein binding being cell cycle-dependent in the came of the CDE. In addition, it was demonstrated that all 3 promoters are deregulated by mutation of the CDE (Table 1). When the cdc25C, cyclin A and cdc2 sequences were compared, it was clear that there was also a remarkable similarity in the region immediately 3' of the CDE (cell cycle genes homology region; CHR) (FIG. 5, SEQ ID NOS 2–7). Although this region is functionally as important as CDZ (Table 1), it is not visible in the in-vivo DMS footprinting experiments. A possible explanation to this is an interaction of the factor with the minor groove of the DNA. Results from electrophoretic mobility shift assay (ENSA) experiments indicate that CDE and CHR jointly bind a protein complex, the CDF. These observations indicate that the CDF-mediated repression of glutaminerich activators is a frequently occurring mechanism in cell cycle-regulated transcription.

However, it is apparently not only the CDE-CHR region which is of importance for regulating the cdc25C promoter but also one of the initiation sites (position +1) within the nucleotide sequence of the basal promoter (positions $\leq -20$ to $\geq +30$, see FIG. 1, SEQ ID NO:1). Mutations in this region, which includes the in-vitro binding site for YY-1 (Seto and Shenk, Nature 354, 241 (1991), Usheva and Shenk, Cell 76, 1115 (1994)) lead to complete deregulation. In view of the proximity of the CDE-CHR to the basal promoter, it is consequently very probable that the CDF interacts with the basal transcription complex.

4.2. Description of the activator sequence

An activator sequence (UAS=upstream activator sequence) is to be understood to be a nucleotide sequence (promoter sequence or enhancer sequence) with which transcription factors, which are formed or are active in the target cell, interact. The CMV enhancer, the CMV promoter (EP 0173. 177.B1), the SV40 promoter, or any other promoter sequence or enhancer sequence known to the skilled person, can be used as an activator sequence.

Within the meaning of this invention, however, the preferred activator sequences include gene-regulatory sequences or elements from genes which encode proteins which are formed, in particular, in cells of the hematopoietic system, in activated lymphocytes, in activated synovial cells or macrophages, in virus-infected cells or in leukemia cells.

4.3. Description of the active substance

The active substance is to be understood to be the DNA for a protein which is to bring about the therapeutic effect, i.e. the curing of the disease of the immune system, and to the site of formation. The choice of the nucleotide sequences for the activator sequence and the active substance depends on the target cell and the active substance which is desired.

4.4. Preparation of the plasmid or vector

The novel DNA construct is made into a complete vector in a manner with which the skilled person is familiar; thus, for example, it is inserted into a viral vector (in this regard, see D. Jolly, Cancer Gene Therapy 1, 51 (1994)), or used as a plasmid. Viral vectors or plasmids can be complexed with colloidal dispersions, for example with liposomes (Farhood et al., Annals of the New York Academy of Sciences 716, 23 (1994)) or with a polylysine/ligand conjugate (Curiel et al., Annals of the New York Academy of Sciences 716, 36 (1994)).

4.5. Supplementation with a ligand

Viral or non-viral vectors of this nature can be supplemented with a ligand which has binding affinity for a membrane structure on the selected target cell. The choice of the ligand consequently depends on the choice of the target cell.

The novel active compound is described in more detail in the following examples.

5) Active Compound for Remedying the Deficient Formation of Blood Cells 5.1. Choice of the activator sequence for hematopoietic cells Within the meaning of the present invention, a gene-regulatory sequence or an element from a gene which encodes a protein which is particularly strongly or selectively expressed in hematopoietic cells is preferably used as the activator sequence. Such gene-regulatory sequences include promoter sequences for genes of a cytokine or of its receptor, whose expression in the immature hematopoietic cells (or in neighboring cells, for example the stroma) takes place prior to the subsequent cytokine, which exerts an effect on the hematopoietic cells and which is desired as the active substance. The following are examples of such cytokines which exert an effect on immature hematopoietic cells stem cell factor (Martin et al., Cell 63, 203 (1990)), which precedes all the hematopoietic factors (McNiece et al., Exp. Haemtol. 19, 226 (1991))

IL-1 (Durum et al., Ann. Rev. Immunol. 3, 263 (1985))

IL-3 (Clark-Lewis et al., J. Biol. Chem. 259, 7488 (1984), Oster et al., Int. J. Cell Clon. 9, 5 (1991))

IL-6 (Mizel, FASEB J. 3, 2379 (1989))

GM-CSF (Gasson, Blood 6, 1131 (1991), Dunlop et al., AntiCancer Drugs 2, 327 (1991))

The promoter sequences for these cytokines and their receptors can be obtained from the following papers:

stem cell factor receptor (Hamamoto et al., Jap. J. Cancer Res. 84, 1136 (1993))

stem cell factor (Szcylik et al., J. Exp. Med. 178, 997 (1993), Bowen et al., Leukemia 7, 1883 (1993), Yamamoto et al., Jp. J. Cancer Res. 84, 11 (1993))

IL-1α

(Hangen et al., Mol. Carcinog. 2, 68 (1986), Turner et al., J. Immnuol. 143, 3556), Mori et al., Blood 84, 1688 (1994))

IL-1 receptor (Ye et al., PNAS USA 90, 2295 (1993))

IL-3

(Mathey-Prevot et al., PNAS USA 87, 5046 (1990), Cameron et al., Blood 83, 2851 (1994), Arai et al., Lymphokine Res. 9, 551 (1990))

IL-3 receptor ( subunit)

(Miyajima et al., Blood 85, 1246 (1995), Rapaport et al., Gene 137, 333 (1993), Kosugi et al., BBRC 208, 360 (1995))

IL-3 receptor (β subunit)

(Gorman et al., J. Biol. Chem. 267, 15842 (1992), Kitamura et al., Cell 66, 1165 (1991), Hayashida et al., PNAS USA 87, 9655 (1990))

IL-6

(Yukasawa et al., EMBO J. 6, 2939 (1987), Lu et al., J. Biol. Chem. 270, 9748 (1995), Ray et al., PNAS 85, 6701 (1988), Droogmans et al., DNA-Sequence 3, 115 (1992), Mori et al., Blood 84, 2904 (1994), Liberman et al., Mol. Cell. Biol. 10, 2327 (1990), Ishiki et al., Mol. Cell. Biol. 10, 2757 (1990), Gruss et al., Blood 80, 2563 (1992))

IL-6 receptor
(Yamasaki et al., Science 241, 825 (1988), Mullberg et al., J. Immunol. 152, 4958 (1994))
GM-CSF
(Nimer et al., Mol. Cell. Biol. 10, 6084 (1990), Staynow et al., PNAS USA 92, 3606), Koyano-Nakayawa et al., Int. Immunol. 5, 345 (1993), Ye et al., Nucl. Acids Res. 22, 5672 (1994))
GM-CSF receptor (a chain)
(Nakagawa et al., J. Biol. Chem. 269, 10905 (1994))
interferon regulatory factor (IRF-1)
The promoter of IRF-1 is activated equally much by IL-6 as by IFN-γ or IFNβ.
(Harrock et al., EMBO J. 13, 1942 (1994))

5.2. Choice of the active substance for hematopoietic cells

Within the meaning of the invention, an active substance is to be understood to mean a DNA sequence whose expressed protein brings about the proliferation and/or differentiation of blood cells.

The following are examples of active substances which are to be selected in dependence on the type of blood cell deficiency:

Active substance for anemia:
DNA sequence for erythropoietin (Jacobs et al., Nature 313, 806 (1985), Lin et al., PNAS 82, 7580 (1985), Krantz, Blood 77, 419 (1991), Dube et al., J. Biol. Chem. 263, 17516 (1988)

Active substance for leukopenia:
DNA sequence for G-CSF (Nagata et al., EMBO J. 5, 575 (1986), Nagata et al., Nature 319, 415 (1986), Souza et al., Science 232, 61 (1986)) or for GM-CSF (Gough et al., Nature 309, 763 (1984), Nicola et al., J. Biol. Chem. 254, 5290 (1979), Wong et al., Science 228, 810 (1985))

Active substance for thrombocytopenia:
DNA for IL-3 (Yang et al., Cell 47, 3 (1986)
DNA for leukemia inhibitory factor (LIF) (Metcalf, Int. J. Cell Clon. 9, 85 (1991), Sutherland et al., Leuk. 3, 9 (1989), Gough et al., PNAS USA 85, 2623 (1988), Gough et al., Ciba Found. Symp. 167, 24 (1992), Stahl et al., J. Biol. Chem. 265, 8833 (1990), Rathjan et al., Cell 62, 1105 (1990))
DNA sequence for IL-11 (Kawashima et al., FEBS Lett. 283, 199 (1991), Paul et al., PNAS 87, 7512 (1990)
and/or
DNA for thrombopoietin (de Sauvage at al., Nature 369, 533 (1994), Kaushansky et al., Nature 369, 568 (1994), Wendling at al., Nature 369, 571 (1994)

However, within the meaning of the invention, DNA sequences of fusion proteins formed between the cited cytokines and growth factors or the extra-cellular moiety of the receptors, on the one hand, and the Fc moiety of human immunoglobulin, on the other hand, can also be used as the active substance. DNA sequences of this nature, and their preparation, have been described in EPA 0464 633 A1.

5.3. Combination of identical or different active substances for hematopoietic cells The invention additionally relates to an active compound in which a combination of the DNA sequences of several identical active substances (A,A) or different active substances (A,B) is present. For expressing the two DNA sequences, the cDNA of an internal ribosome entry site (IRES) is preferably intercalated as a regulatory element.

Such IRES have, for example, been described by Montford and Smith (TIG 11, 179 (1995), Kaufman et al., Nucl. Acids Res. 19, 4485 (1991), Morgan et al., Nucl. Acids Res. 20, 1293 (1992), Dirks et al., Gene 128, 247 (1993), Pelletier and Sonenberg, Nature 334, 320 (1988) and Sugitomo et al., Bio-Techn. 12, 694 (1994).

For example, the cDNA of the IRES sequence of poliovirus (positions ≦140 to ≧630 of the 5' UTR (Pelletier and Sonenberg, Nature 334, 320 (1988)) can be used to link the DNA of antiinflammatory substance A (at the 3' end) and the DNA of anti-inflammatory substance B (at the 5' terminus).

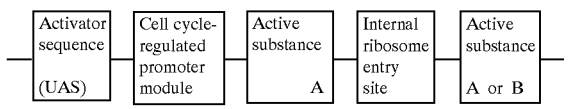

Depending on the combination employed, an active compound of this nature exhibits either an additive (A+A, A+B) or synergistic (A+B) effect.

5.4. Choice of the ligand for hematopoietic cells

The aim should be to bring the active compound to the target cell or to cells adjoining the target cell. For this purpose, viral or non-viral vectors can be provided with a ligand. The ligand should preferably bind with membrane structures or membrane receptors on undifferentiated or only slightly differentiated blood cells.

The ligands include antibodies or antibody fragments which are directed against receptors which are expressed on blood cells which are only slightly differentiated.

Antibodies of this nature have, for example, been described for the following receptors:

stem cell factor receptor
(Blechman et al., Cell 80, 103 (1995), Oez et al., Eur. Cytokine Netw. 4, 293 (1993))
IL-1 receptor (type I)
(McMahan et al., EMBO J. 10, 2821 (1991), Giri et al., Cytokine 4, 18 (1992)
IL-1 receptor (type II)
(Scapigliati et al., J. Immunol. Methods 138, 31 (1991))
IL-3 receptor α
(Sato et al., Blood 82, 752 (1993))
IL-3 receptor β
(Korpelainen et al., Blood 86, 176 (1995))
IL-6 receptor
(Daveau et al., Eur. Cytokine Netw. 5, 601 (1994), Sui et al., PNAS USA 92, 2859 (1995), Goto et al., Jpn. J. Cancer Res. 85, 958 (1994))
GM-CSF receptor
(Nicola et al., Blood 82, 1724 (1993))

In addition, the ligands also include monoclonal or polyclonal antibodies or antibody fragments which, by way of their constant domains, bind to Fc-γ receptors of immune cells (Rojanasakul et al., Pharm. Res. 11, 1731 (1994)).

The murine monoclonal antibodies are preferably to be employed in humanized form. The humanization is effected in the manner described by Winter et al. (Nature 349, 293 (1991)) and Hoogenbooms et al. (Rev. Tr. Transfus. Haemobiol. 36, 19 (1993)). Antibody fragments are prepared in accordance with the state of the art, for example in the manner described by Winter et al. (Nature 349, 293 (1991), Hoogenboom et al. (Rev. Tr. Transfus. Hemobiol. 36, 19 (1993), Girol (Mol. Immunol. 28, 1379 (1991) and Huston et al. (Int. Rev. Immunol. 10, 195 (1993).

The ligands additionally include all substances which bind to membrane structures or membrane receptors on the surface of blood cells which are only slightly differentiated. By way of example, these substances include growth factors, such as SCF, IL-1, IL-3, IL-6, GM-CSF or their fragments or constituent sequences thereof, which bind to receptors which are expressed by cells of this nature.

5.5. Preparation of the active compound for hemapoietic cells

The preparation of the novel active compound is described in more detail with the aid of the following examples:

a) Construction of the chimeric Dromoter SCF-receptor-CDE-CHR-Inr

Figure 6:
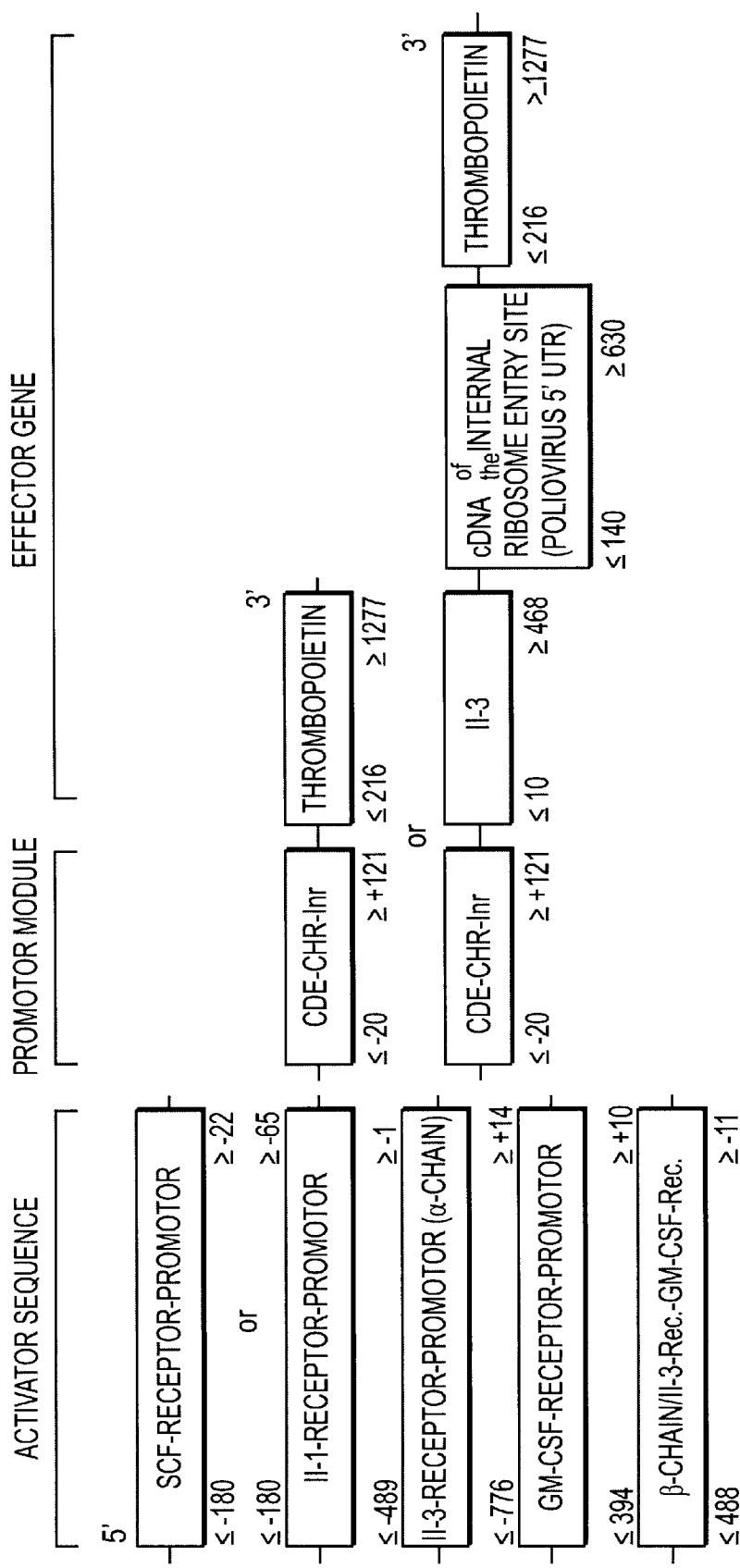

The human SCF receptor promoter (position $\leq-180$ to $\geq-22$, Yamamoto et al., Jpn. J. Cancer Res. 84, 1136 (1993)), or a variant which is truncated by the length of the TATA box (position $\leq-180$ to $\geq-65$), are linked, at their 3' end, to the 5' terminus of the CDE-CHR-Inr module (position $\leq-20$ to $\geq+121$) of the human cdc25C gene (Lucibello et al., EMBO J., 14, 132 (1995)) (FIG. 6). The linking is effected using enzymes which are known to the skilled person and which are commercially available.

b) Construction of a plasmid which contains the chimeric promoter SCF-receptor-CDE-CHR-Inr in the central component of the active compound The described chimeric SCF-receptor-repressor module transcription unit is linked, at its 3' end, to the 5' terminus of a DNA which contains the complete coding region of thromopoietin (position $\leq$p216 to $\geq$1277) (de Sauvage et al., Nature 369, 533 (1994)) (FIG. 6). This DNA also contains the signal sequence which is necessary for secretion. Transcription control units, and the DNA for thrombopoietin, are cloned into pUC18/19 or Bluescript-derived plasmid vectors, which can be used directly, or in colloidal dispersion systems, for in-vivo administration. Alternatively, the chimeric genes can be transferred into viral vectors, or other suitable vectors, and injected.

c) Construction of the chimeric promoter IL-1-receptor-CDE-CHR-Inr

The himan IL-1 receptor promoter (pos. $\leq-489$ to $\geq-1$, Ye et al., PNAS USA 30, 2295 (1993)) is linked, at its 3' end, to the 5' terminus of the CDZ-CHR-Inr module of the human cdc25C gene (pos. $\leq-20$ to $\geq+121$ of the sequence published by Lucibello et al., EMBO J. 14, 132 (1995)) (see FIG. 6). The linking is effected using enzymes which are known to the skilled person and which are commercially available.

d) Construction of a plasmid which contains the chimeric promoter IL-1-receptor-CDE-CHR-Inr in the central component of the active compound The chimeric IL-1 receptor repressor module transcription control unit described in c) is linked, at its 3' end, to the 5' terminus of a DNA which contains the complete coding region of thrombopoietin (see FIG. 6). This DNA also contains the signal sequence which is required for secretion. Transcription control units, and the DNA for tissue plaminogen activator, are cloned into pUC18/19 or Bluescrip- derived plasmid vectors, which can be used, directly or in colloidal dispersion system, for in-vivo administration. Alternatively, the chimeric genes can be transferred into viral vectors, or other suitable vectors, and injected.

e) Construction of a plasmid which contains two genes for active substances

The SCF receptor-CDE-CHR-Inr transcription unit which is described in a) is linked, at its 3' end, to the 5' end of the DNA for interleukin 3 (position $\leq 10$ to $\geq 468$, Yang et al., Cell 47, 3 (1986)). The linking is effected using enzymes which are known to the skilled person and which are commercially available.

The 3'end of the DNA for IL-3 is now linked to the 5' end of the cDNA of the internal ribosome entry site (position $\leq 140$ to $\geq 630$; Pelletier and Sonnenberg, Nature 334, 320 (1988)), and their 3' end is subsequently linked to the 5' end of the DNA for thrombopoietin (see FIG. 6). The active compound which has been prepared in this way is then cloned into pUC18/19 or into Bluescript-derived plasmid vectors, which can be used, directly or in colloidal dispersion systems, for in-vivo administration. Alternatively, the chimeric genes can be transferred into viral vectors, or other suitable vectors, and injected.

f) Construction of other transcription units

The possibility of combining the IL-3 receptor ($\alpha$ chain) promoter, the GM-CSF receptor ($\alpha$ chain) promoter or the GM-CSF receptor ($\beta$ chain) promoter with the repressor module CDE-CHR-Inr and the effector genes which have already been mentioned is depicted in FIG. 6.

6. Active Compound for the Therapy of Autoimmune Diseases, Allergies and Inflammation, and for Preventing Organ rejections 6.1. Choice of the activator sequence for, inter alia, autoimmune diseases The promoter sequences of the genes for those proteins which are formed to an increased extent in macrophages and/or lymphocytes during the immune reaction are to be used as activator sequences. The following are examples of proteins of this nature IL-1 (Bensi et al., Gene 52, 95 (1987), Fibbe et al., Blut 59, 147 (1989))

IL-1 receptor (Colotta et al., Immunol. Today 15, 562 (1994), Sims et al., Clin. Immunol. Immunopath. 72, 9 (1994), Ye et al., PNAS USA 90, 2295 (1993))

IL-2 (Jansen et al., CII 39, 207 (1994), Ohbo et al., J. Biol. Chem. 270, 7479 (1995))

IL-2 receptor (Semenzato et al., Int. J. Clin Lab. Rem. 22, 133 (1992))

IFN γ (Kirchner, DKW 111, 64 (1986), Lehman et al., J. Immunol. 153, 165 (1994))

IL-4 (Paul, Blood 77, 1859 (1991), te Velde et al., Blood 76, 1392 (1990))

IL-4 receptor (Vallenga et al., Leukemia 7, 1131 (1993), Galizzi et al., int. Immunol. 2, 669 (1990))

IL-3 (Frend, Int. J. Immunopharm. 14, 421 (1992))

IL-5 (Azuma et al., Nucl. Acid Res. 14, 9149 (1986), Yokota et al., PNAS 84, 7388 (1987))

IL-6 (Brack et al., Int. J. Clin. Lab. Res. 22, 143 (1992))

LIF (Metcalf, Int. J. Cell Clon. 9, 95 (1991), Samal, BBA 1260, 27 (1995))

IL-7 (Joshi et al., 21, 681 (1991))

IL-10 (Benjamin et al., Leuk. Lymph. 12, 205 (1994), Fluchiger et al., J. Exp. Med. 179, 91 (1994))

IL-11 (Yang et al., Biofactors 4, 15 (1992))

IL-12 (Kiniwa et al., J. Clin. Invest. 90, 262 (1992), Gatelay, Cancer Invest. 11, 500 (1993))

IL-13 (Punnonen et al., PNAS 90, 3730 (1993), Muzio et al., Blood 83, 1738 (1994))

GM-CSF (Metcalf, Cancer 15, 2185 (1990))

GM-CSF receptor (Nakagawa et al., J. Biol. Chem. 269, 10905 (1994))

Itegrin beta 2 proteins (LFA-1, MAC-1 and p150/95) (Nueda et al., J. Biol. Chem. 268, 19305 (1993))

Promoter sequences for these proteins were described as follow.

IL-1 receptor (Ye et al., PNAS USA 90, 2295 (1993))

IL-1α (Hangon et al., Mol. Carbinog. 2, 68 (1986), Turner et al., J. Immunol. 143, 3556 (1989), Mori et al., Blood 84, 1688 (1994))

IL-1β
(Fenton et al., J. Immunol. 138, 3972 (1987), Bensi et al., Cell Growth Diff. 1, 491 (1990), Turner et al., J. Immunol. 143, 3556 (1989), Hiscott et al., Mol. Cell. Biol. 13, 6231 (1993))

IL-2
(Fujita et al., Cell 46, 401 (1986), Hama et al., J. Exp. Med. 181, 1217 (1995), Kant et al., Lymph. Rec. Interact. 179 (1989), Kamps et al., Mol. Cell. Biol. 10, 5464 (1990), Williams et al., J. Immunol. 141, 662 (1988), Brunvand, FASEB J. 6, A998 (1992), Matsui et al., Lymphokines 12, 1 (1985), Tanaguchi et al., Nature 302, 305 (1983))

Il-2 receptor
(Ohbo et al., J. Biol. Chem. 270, 7479 (1995), Shibuya et al., Nucl. Acids Res. 18, 3697 (1990), Lin et al., Mol. Cell. Biol. 13, 6201 (1993), Semenzato et al., Int. J. Clin. Lab. Res. 22, 133 (1992))

IL-3
(Mathey-Prevot et al., PNAS USA 87, 5046 (1990), Cameron et al., Blood 83, 2851 (1994), Arai et al., Lymphokine Rem. 9, 551 (1990))

IL-3 receptor (α subunit)
(Miyajima et al., Blood 85, 1246 (1995), Rapaport et al., Gene 137, 333 (1993), Kosugi et al., BBRC 208, 360 (1995))

IL-3 receptor (β subunit)
(Gorman et al., J. Biol. Chem. 267, 15842 (1992), Kitamura et al., Cell 66, 1165 (1991), Hayashida et al., PNAS USA 87, 9655 (1990))

IL-4
(Rooney et al., EMBO J. 13, 625 (1994), Hama et al., J. Exp. Med. 181, 1217 (1395), Li-Weber et al., J. Immunol. 153, 4122 (1994), 148, 1913 (1992), Min et al., J. Immunol. 148, 1913 (1992), Abe et al., PNAS 89, 2864 (1992))

IL-4 receptor
(Beckmann et al., Chem. Immunol. 51, 107 (1992), Ohara et al., PNAS 85, 8221 (1988))

IL-5
(Lee et al., J. Allerg. Clin. Immunol. 94, 594 (1994), Kauhansky et al., J. Immunol. 152, 1812 (1994), Staynov et al., PNAS USA 92, 3606 (1995))

IL-6
(Lu et al., J. Biol. Chem. 270, 9748 (1995), Gruss et al., Blood 80, 2563 (1992), Ray et al., PNAS 85, 6701 (1988), Droogmans et al., DNA-Sequence 3, 115 (1992), Mori et al., Blood 84, 2904 (1994), Liberman et al., Mol Cell. Biol. 10, 2327 (1990), Ishiki at al., Mol. Cell. Biol. 10, 2757 (1990))

Interferon regulatory factor 1 (IRF-1)
(The promoter of IRF-1 is activated equally much by IL-6 as by IFN-γ or IFNβ. (Harrock et al., EMBO J. 13, 1942 (1994))

IFN-γ responsive promoter
(Lamb et al., Blood 83, 2063 (1994))

IL-7
(Pleiman et al., Mol. Cell. Biol. 11, 3052 (1991), Lapton et al., J. Immunol. 144, 3592 (1990))

IL-8
(Chang et al., J. Biol. Chem. 269, 25277 (1994), Sprenger et al., J. Immunol. 153, 2524 (1994))

IL-10
(Kim et al., J. Immunol. 148, 3618 (1992), Platzer et al., DNA Sequence 4, 399 (1994), Kube et al., Cytokine 7, 1 (1995))

IL-11
(Yang et al., J. Biol. Chem. 269, 32732 (1994))

IFN-γ
(Ye et al., J. Biol. Chem. 269, 25728 (1994), Hardy et al., PNAS 82, 8173 (1985))

GM-CSF
(Nimer et al., Mol. Cell. Biol. 10, 6084 (1990), Staynov et al., PNAS USA 92, 3606 (1995), Koyano-Nakayawa et al., Int. Immunol. 5, 345 (1993), Ye et al., Nucl. Acids Res. 22, 5672 (1994))

GM-CSF receptor (α chain)
(Nakagawa et al., J. Biol. Chem. 269, 10905 (1994))

IL-13
(Staynov et al., PNAS USA 92, 3606 (1995)

LIF
(Gough et al., Ciba Found. Symp. 167, 24 (1992), Stahl et al., Cytokine 5, 386 (1993))

Macrophage colony stimulating factor (M-CSF) receptor
(Yue et al., Mol. Cell. Biol. 13, 3191 (1993), Zhang et al., Mol. Cell. Biol. 14, 373 (1994))

Type I and II macrophage scavenger receptors
(Moulton et al., Mol. Cell. Biol. 14, 4408 (1994))

MAC-1 (leukocyte function antigen)
(Dziennis et al., Blood 85, 319 (1995), Bauer et al., Hum. Gene Ther. 5, 709 (1994), Hickstein et al., PNAS USA 89, 2105 (1992))

LFA-1α (leukocyte function antigen)
(Nueda et al., J. Biol. Chem. 268, 19305 (1993), Agura et al., Blood 79, 602 (1992), Cornwell et al., PNAS USA 90, 4221 (1993))

p150,95 (leukocyte function antigen)
(Noti et al., DNA and Cell Biol. 11, 123 (1992), Lopezcabrera et al., J. Biol. Chem. 268, 1187 (1993))

The listing of the promoters for cytokines and cytokine receptors is only by way of example and should not be understood to mean a restriction.

The following promoter sequences can, for example, be selected in association with the different autoimmune diseases:

in association with allergies:
the promoter sequences for IL-1, IL-1 receptor, IL-2, IL-2 receptor, IL-4 or IL-4 receptor in association with cell-mediated or antibody-mediated autoimmune diseases:
the promoter sequences for IL-1, IL-1 receptor, IL-2 or IL-2 receptor for preventing organ rejection:
the promoter sequences for IL-1, IL-1 receptor, IL-2 or IL-2 receptor 6.2. Choice of the active substance for, inter alia, autoimmune diseases Within the meaning of the invention, the active substance is the DNA sequence for a cytokine, a chemokine, a growth factor, or one of their inhibitors, an antibody or an enzyme. The choice of the active substance depends on the primary disease which is to be treated and on the activator sequence which is selected. For example, one of the following active substances can be selected in association with the following diseases:

a) Active substance for therapy of allergies

DNA sequence for IFNα (Henco et al., J. Mol. Biol. 185, 227 (1985), Pestka et al., Ann. Rev. Biochem. 56, 727 (1987), Weissmann et al., Phil. Trans. R. Soc. Lond. B299 7 (1982), Goeddel et al., Nature 290, 20 (1981)) or IFNβ

(Sen et al., J. Biol. Chem. 267, 5017 (1992), Mark et al., EP 192 811, EP 234 599, US 45 88 585) or IFN-γ (Gray et al., Nature 295, 503 (1982), Yip et al., PNAS USA 79, 1820 (1982), Rinderknecht et al., J. Biol. Chem. 259, 6790 (1984)) or IL-10

(Moore et al., Science 248, 1230 (1990), Vieira et al., PNAS USA 88, 1172 (1991), Kim et al., J. Immunol. 148 3618 (1992)) or soluble IL-4 receptors (Idzerda et al., J. Exp. Med. 171, 861 (1990), EPA 0419 091 A1, Foxwell, Eur. J. Immunol. 19, 1637 (1989), Garrone et al., Eur. J. Immunol. 21, 1365 (1991), Gallizzi et al., Int. Immunol. 2, 226 (1990), Park et al., J. Exp. Med. 166, 476 (1987)) or IL-12

(Kobayashi et al., J. Exp. Med. 170, 827 (1989), Gabler et al., PNAS 88, 4143 (1991), Gately et al., J. Immunol. 147, 874 (1991), Schoenhaut et al., J. Immunol. 148, 3433 (1992), (Wolf et al., J. Immunol. 146, 3074 (1991)) or TGFβ

(Massague, Ann. Rev. Cell. Biol. 6, 597 (1990), Kondiah et al., J. Biol. Chem. 265, 1089 (1990), Garnier et al., J. Molec. Biol. 120, 97 (1978))

b) Active substance for preventing the rejection of transplanted organs

DNA sequence for IL-10 (Moore et al., Science 248, 1230 (1990), Vieira et al., PNASUSA 88, 1172 (1991), Kim et al., J. Immunol. 148, 3618 (1992)) or TGFβ

(Massague, Ann. Rev. Cell Biol. 6, 597 (1990), Kondiah et al., J. Biol. Chem. 265, 1089 (1990), Garnier et al., J. Mol. Biol. 120, 97 (1978) or soluble IL-1 receptors (Sims et al., PNAS USA 86, 8946 (1989) (I), Dower et al., J. Exp. Med. 162, 501 (1985), Chizzonite et al., PNAS 86, 8029 (1989)), McMahan et al., EMBO J. 10, 2821 (1991) (II), Sims et al., Science 241, 585 (1988)) or soluble IL-2 receptors (Taneguchi et al., Nature 302, 305 (1983), Greene et al., Ann. Rev. Immunol. 4, 69 (1986), Hatakeyama et al., Science 244, 551 (1989), Takeshita et al., Science 257, 379 (1992), Russel et al., Science 262, 1880 (1993)) or IL-1 receptor antagonists (Eisenberg et al., Nature 343, 341 (1990), Carter et al., Nature 344, 633 (1990))

or soluble IL-6 receptors (Mackiewicz et al., Cytokine 7, 142 (1995))

or a DNA sequence for an immuosuppressive antibody or its $V_H$ and $V_L$-containing fragments or its $V_H$ and $V_L$ fragments which are connected via a linker, prepared, for example, in accordance with the methodology described by Marasco et al. (Proc. Natl. Acad. Sci. USA 90, 7889 (1993)). Examples of immuosuppressive antibodies are antibodies which are specific for the T cell receptor or its CD3 complex, antibodies against CD4 or CD8 and, in addition, against the IL-2 receptor (Strom et al., Ann. Rev. Ned. 44, 343 (1993), Scheringer et al., Ann. Hematol. 66, 181 (1993)), the IL-1 receptor or the IL-4 receptor, or against the adhesion molecules CD2, LFA-1, CD28 or CD40 (Olive et al., Drug Carriers Syst. 10, 29 (1993), Wendling et al., J. Rheumatol. 18, 325 (1991), Van der Lubbe et al., Arthritis Rheum. 34, 89 (1991)).

c) Active substance for the therapy of antibody-mediated autoimmune diseases

DNA sequence for TGFβ (Massague, Ann. Rev. Cell Biol. 6, 597 (1990), Kondiah et al., J. Biol. Chem. 265, 1089 (1990), Garnier et al., J. Molec. Biol. 120, 97 (1978)) or IFNα

(Henco et al., J. Mol. Biol. 185, 227 (1985), Pestka et al., Ann. Rev. Biochem. 56, 727 (1987), Weissmann et al., Phil. Trans. R. Soc. Lond. B299, 7 (1982), Goeddel et al., Nature 290, 20 (1981), Sen et al., J. Biol. Chem. 267 5017 (1992), Mark et al., EP 192 911, EP 234 599, US 45 88 585) or IFNβ

(Sen et al., J. Biol. Chem. 267, 5017 (1992), Mark et al., EP 192 811, EP 234 599, US 45 88 585) or IFN-γ

(Gray et al., Nature 295, 503 (1982), Yip et al., PNAS USA 79, 1820 (1982), Rinderknecht et al., J. Biol. Chem. 259, 6790 (1984)) or IL-12

(Kobayashi et al., J. Exp Mod. 170, 827 (1989), Gabler et al., PNAS 88, 4143 (1991), Gately et al., (J. Immunol. 147, 874 (1991), Schoenhaut et al., J. Immunol. 148, 3433 (1992), Wolf et al., J. Immunol. 146, 3074 (1991)) or soluble IL-4 receptors (Idzerda et al., J. Exp. Med. 171, 861 (1990), EPA 0419 091 A1, Foxwell, Eur. J. Immunol. 19, 1637 (1989), Garrone et al., Eur. J. Immunol. 21, 1365 (1991), Gallizzi et al., Int. Immunol. 2, 226 (1990), Park et al., J. Exp Med. 166, 476 (1981)) or soluble IL-6 receptors (Machiewicz et al., Cytokine 7, 142 (1995)) or DNA sequence for an immunosuppressive antibody (see Section 6.2.b) or its $V_H$-containing and $V_L$-Containing fragments, or its $V_H$ and $V_L$ fragments which are connected via a linker, prepared, for example, in accordance with the methodology described by Marasco et al. (Proc. Natl. Acad. Sci. USA 90, 7889 (1993))

d) Active substance for DNA sequence for IL-6 the therapy of cell- (Wong et al. , Immunol. mediated autoimmune Today 9, 137 (1988), disease Brakenhoff et al., Immunol. 143, 1175 (1989), Yasukawa et al., EMBO J. 6, 2939 (1987)) or IL-9 (Yang et al., Blood 74, 1880 (1989), Mock et al., Immunogenetics 31, 265 (1990)) or IL-10 (Moore et al., Science 248, 1230 (1990), Vieira et al., PNAS USA 88, 1172 (1991), Kim et al., J. Immunol. 148, 3618 (1992)) or IL-13 (McKenzie et al., PNAS 90, 3735 (1993), Minty et al., Nature 362, 248 (1993), McKenzie et al., J. Immunol. 150, 5436 (1993)) or TFNα(Beutler et al., Nature 320, 584 (1986), Kriegler et al., Cell 53, 45 (1988)) or IL-4 (Lee et al., PNAS 83, 2061 (1986), Paul, Blood 77, 1859 (1991), Yokota et al., PNAS USA 83, 5894 (1986), von Leuven et al., Blood 73, 1142 (1989), Arai et al. , J. Immunol. 142, 274 (1989)) or TNFβ

(Gray et al., Nature 312, 721 (1984), Li et al., J. Immunol. 138, 4496 (1987), Aggarwal et al., J. Biol. Chem. 260, 2334 (1985), or a DNA sequence for an immunosuppressive antibody its $V_H$- and $V_L$-containing fragments its $V_H$ and $V_L$ fragments which are connected via a linker (see Section 6.2.b).

When receptors are selected as the active substance, their extracellular moieties are to be used.

However, within the meaning of the invention, DNA sequences of fusion proteins formed between the listed cytokines and growth factors, or the extracellular moiety of the particular receptors, on the one hand, and the Fc moiety of human immunoglobulin, on the other hand, can also be used as the active substance. DNA sequences of this nature, and their preparation, have been described in EP 0464 533 A1.

e) Inhibiting proteins

Within the meaning of the invention, however, an active substance is also to be understood as being a cell cycle inhibitor. Within the meaning of the invention, a cell cycle inhibitor is a DNA sequence whose expressed protein inhibits the proliferation of cells. These cell cycle inhibitors include, for example, the DNA sequences for the following proteins:

the retinoblastoma protein (pRb=p110) or the related p107 and p130 proteins (La Thangue, Curr. Opin. Cell Biol. 6, 443 (1994))

the p53 protein (Prives et al., Genes Dev. 7, 529 (1993))

the p21 (WAF-1) protein (El-Deiry et al., Cell 75, 817 (1993))

the p16 protein (Serrano et al., Nature 366, 704 (1993), et al., Science 264, 436 (1994), Norbori et al., Nature 368, 753 (1994))

other cdK inhibitors (Review in Pines, TIBS 19, 143 (1995))

the GADD45 protein (Papathanasiou et al., Mol. Cell. Biol. 11, 1009 (1991), Smith et al., Science 266, 1376 (1994))

the bak protein (Farrow et al., Nature 374, 731 (1995), Chittenden et al., Nature 374, 733 (1995), Kiefer et al., Nature 374, 736 (1995)).

In order to prevent rapid intracellular inactivation of the cell cycle inhibitors, those genes are preferably to be used which possess mutations for the inactivation sites of the expressed proteins without the function of these proteins thereby being impaired.

The retinoblastoma protein (pRb/p110) and the related p107 and p130 proteins are inactivated by phosphorylation. Consequently, preference is given to using a pRb/p110 cDNA sequence, p107 cDNA sequence or p130 cDNA sequence which is point-mutated in such a way that the phosphorylation sites of the encoded protein are replaced with amino acids which cannot be phosphorylated.

While the cDNA sequence for the retinoblastoma protein (p110) is altered, in accordance with Hamel et al., (Mol. Cell Biol. 12, 3431 (1992)) so that it can no longer be phosphorylated by replacing the amino acids in positions 246, 350, 601, 605, 780, 786, 787, 800 and 804, its binding activity with the large T antigen is not impaired. For example, the amino acids Thr-246, Ser-601, Ser-605, Ser-780, Ser-786, Ser-787 and Ser-800 are replaced with Ala, the amino acid Thr-350 with Arg and the amino acid Ser-804 with Glu.

The DNA sequence for the p107 protein or the p130 protein is mutated in an analogous manner.

The p53 protein is inactivated in the cell either by binding to special proteins, such as MDM2, or by oligomerization of the p53 by way of the dephosphorylated C-terminal serine 392 (Schikawa et al., Leukemia and Lymphoma 11, 21 (1993) and Brown, Annals of Oncology 4, 623 (1993)). Consequently, a DNA sequence for a p53 protein is preferably used which has been truncated C-terminally by removing the serine 392.

f) Cytostatic or cytotoxic proteins

A cell cycle inhibitor is additionally to be understood to be a DNA sequence which expresses a cytostatic or cytotoxic protein.

The following are examples of proteins of this nature:

perforin (Lin et al., Immunol. Today 16, 194 (1995))

granzyme (Smyth et al., Immunol. Today 16, 202 (1995))

TNF (Porter, TibTech 9, 158 Sidhu et al., Pharmc. Ther. 57, 79 (1993)), especially TNFα (Beutler et al., Nature 320, 584 (1986), Kriegler et al., Cell 53, 45 (1988)

TNFβ (Gray et al., Nature 312, 721 (1984), Li et al., J. Immunol. 138, 4496 (1987), Aggarwal et al., J. Biol. Chem. 260, 2334 (1985))

g) Enzymes for activating Precursors of cytostatic agents

However, a cell cycle inhibitor is also to be understood as being the DA sequence for an enzyme which converts an inactive precursor of a cytostatic agent into a cytostatic agent.

Enzymes of this nature, which cleave inactive precursor substances (prodrugs) into active cytostatic agents (drugs), and the relevant prodrugs and drugs in each case, have already been reviewed by Deonarain et al. Br. J. Cancer 70, 786 (1994), by Mullen, Pharmac. Ther. 63, 199 (1994) and Harris et al., Gene Ther. 1, 170 (1994)).

For example, the DNA sequence of the following enzymes may be used:

herpes simplex virus thymidine kinase (Garapin et al., PNAS USA 76, 3755 (1979), Vile et al., Cancer Res. 53, 3860 (1993), Wagner et al., PNAS USA 78, 1441 (1981), Moelten et al., Cancer Res. 46, 5276 (1986), J. Natl. Cancer Inst. 82, 297 (1990))

varicella zoster virus thymidine kinase (Huber et al., PNAS USA 88, 8039 (1991), Snoeck, nt. J. Antimicrob. Agents 4, 211 (1994))

bacterial nitroreductase (Michael et al., FEMS Microbiol. Letters 124, 195 (1994), Bryant et al., J. Biol. Chm. 266, 4126 (1991), Watanabe et al., Nucleic Acids Res. 18, 1059 (1990))

bacterial β-glucuronidase (Jefferson et al., PNAS USA 83, 8447 (1986))

vegetable β-glucuronidase from Secale cereale (Schulz et al., Phytochemistry 26, 933 (1987))

human β-glucuronidase (Bosslet et al., Br. J. Cancer 65, 234 (1992), Oshima et al., PNAS USA 84, 685 (1987))

human carboxypeptidame (CB), e.g.

mast cell CB-A (Reynolds et al., J. Clin. Invest. 89, 273 (1992))

pancreatic CB-B (Yamamoto et al., J. Biol. Chem. 267, 2575 (1992), Catasus et al., J. Biol. Chem. 270, 6651 (1995))

bacterial carboxypeptidase (Hamilton et al., J. Bacteriol. 174, 1626 (1992), Osterman et al., J. Protein Chem. 11, 561 (1992))

bacterial β-lactamase (Rodrigues et al., Cancer Res. 55, 63 (1995), Hussain et al., J. Bacteriol. 164, 223 (1985), Coque et al., Embo J. 12, 631 (1993)

bacterial cytosine deaminase (Mullen et al., PNAS USA 89, 33 (1992), Austin et al., Mol. Pharmac. 43, 380 (1993), Danielson et al., Mol. Microbiol. 6, 1335 (1992)

human catalase or peroxidase (Ezurum et al., Nucl. Acids Res. 21, 1607 (1993))

phosphatase, in particular human alkaline phosphatase (Gum et al., Cancer Res. 50, 1085 (1990))

human acid prostate phosphatase (Sharieff et al., Am. J. Hum. Gen. 49, 412 (1991), Song et al., Gene 129, 291 (1993), Tailor et al., Nucl. Acids Res. 18, 4928 (1990))

type 5 acid phosphatase (Gene 130, 201 (1993))

oxidase, in particular human lysyl oxidase (Kimi et al., J. Biol. Chem. 270, 7176 (1995))

human acid D-aminooxidase (Fukui et al., J. Biol. Chem. 267, 18631 (1992))

peroxidase, in particular human gluthatione peroxidase (Chada et al., Genomics 6, 268 (1990), Ishida et al., Nul. Acids Res. 15, 10051 (1987))

human eosinophilic peroxidase (Ten et al., J. Exp. Med. 169, 1757 (1989), Sahamaki et al., J. Biol. Chem. 264, 16828 (1989))

human thyroid peroxidase (Kimura, PNAS USA 84, 5555 (1987)).

In order to facilitate secretion of the cited enzymes, the homologous signal sequence which is in each case containing in the DNA sequence can be replaced by an heterologous signal sequence which improves extracellular secretion.

Thus, the signal sequence of β glucuronidase (DNA position ≦27 to 93; Oshima et al., PNAS 84, 685 (1987)) can, for example, be replaced by the signal frequency for human imunoglobulin (DNA position ≦63 to ≧107; Riechmann et al., Nature 332, 323 (1988)).

In addition, preference should be given to selecting DNAs of those enzymes which, as a result of point mutations, are stored to a lesser extent in lysosomes. Point mutations of this nature have been described, for example, for β-glucuronidase (Shipley et al., J. Biol. Chem. 268, 12193 (1933)).

6.3. Combination of identical or different active substances for, inter alia, autoimmune diseases The invention additionally relates to an active compound in which a combination of the DNA sequences of several identical active substances (A,A) or different active substances (A,B) is present. The cDNA of an internal ribosome entry site (IRES) is preferably intercalated, as a regulatory element, for the purpose of expressing several DNA sequences, for example. IRESs of this nature have been described by Mountford and Smith (TIG 11, 179 (1995), Kaufman et al., Nucl. Acids Res. 19, 4485 (1991), Morgan et al., Nucl. Acids Res. 20, 1293 (1992) and Dirks et al., Gene 129, 247 (1993), Pelletier and Sonenberg, Nature 334, 320 (1988), Sugitomo et al., BioTechn. 12, 694 (1994).

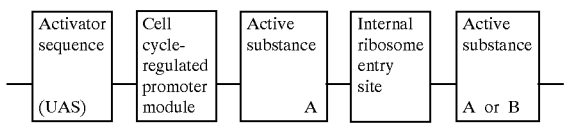

Depending on the combination, an active compound of this nature exhibits either an additive or a synergistic effect within the meaning of the invention.

6.4. Choice of the ligand for, inter alia, autoimmune diseases

Substances which specifically bind to the surface of immune cells (macrophages and lymphocytes) are preferred as ligands for viral and non-viral vectors, for example prepared in colloidal dispersions using polylysine ligand conjugates. These substances include antibodies or antibody fragments which are directed against membrane structures of immune calls, as have been described, for example, by Powelson et al., Biotech. Adv. 11, 725 (1993).

In addition, the ligands also include monoclonal or polyclonal antibodies or antibody fragments which bind, by their constant domains, to Fc-γ receptors or [lacuna] receptors of immune cells (Rojanasakul et al., Pharm. Res. 11, 1731 (1994)). The murine monoclonal antibodies should preferably be employed in humanized form. The humanization is effected in the manner described by Winter et al., (Nature 349, 293 (1991)) and Hoogenbooms et al. (Rev. Tr. Transfus. Hemobiol. 36, 19 (1993)). Antibody fragments are prepared in accordance with the state of the art, for example in the manner described by Winter et al. (Nature 349, 293 (1991)), Hoogenboom et al. (Rev. Tr. Transfus. Hemobiol. 36, 19 (1993)), Girol (Mol. Immunol. 28, 1379 (1991) and Huston et al. (Int. Rev. Immunol. 10, 195 (1993)).

Furthermore, the ligands include all substances which bind to membrane structures or membrane receptors on the surface of Immune cells. These substances include, for example, growth factors, such as cytokines, EGF, TGF, FGF or PDGF, or their fragments or constituent sequences thereof, which bind to receptors which are expressed by cells of this nature.

The ligands also include ligands which bind to cell membrane structures, for example the mannose 6-phosphate receptor on macrophages in spleen, liver, lung and other tissues.

These ligands and membrane structures are clearly described in Perales et al., Eur. J. Biochem. 226, 255 (1994).

6.5. Preparation of the active compound for, inter alia, autoimmune diseases

The preparation of the novel active compound is described in more detail with the aid of the following examples:

a) Construction of the chimeric Dromoter IL-2-CDE-CHR-Inr

Figure 7:
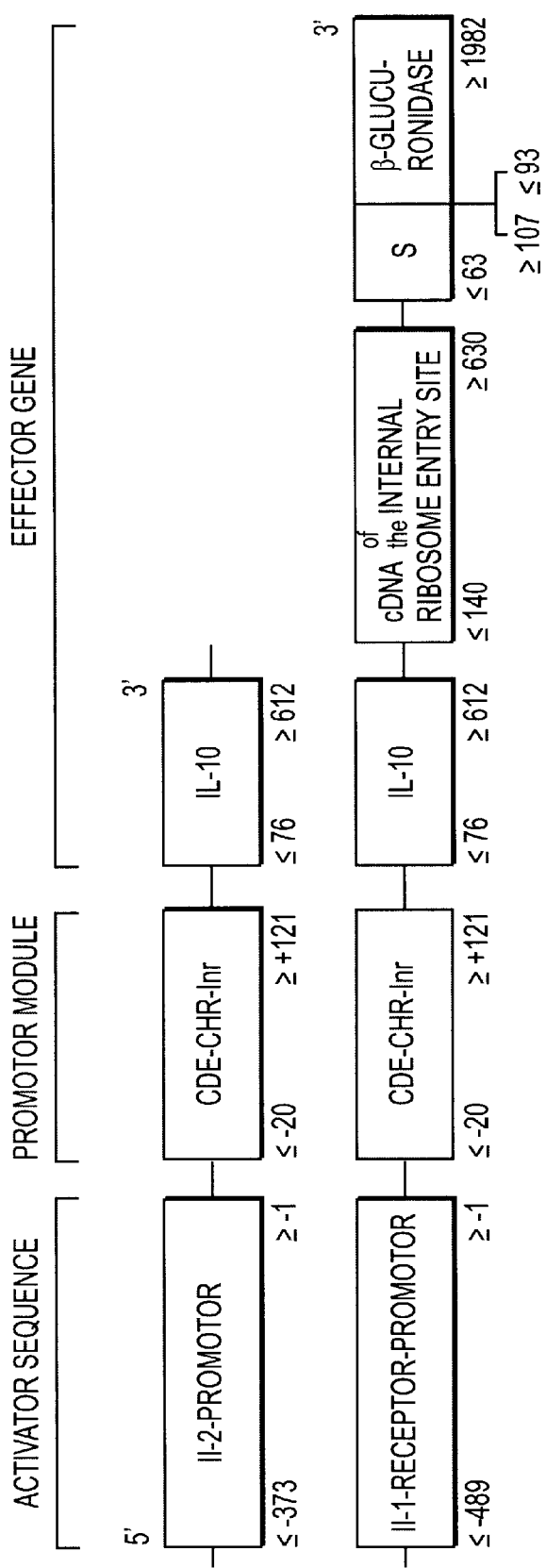

The human IL-2 promoter (position ≦-373 to ≧-1, Williams et al., J. Immunol. 141, 662 (1988)) is linked, at its 3' end, to the 5' terminus of the CDE-CHR-Inr module (position ≦-20 to ≧+121) of the human cdc25C gene (Luci-bello et al., EMO J., 14, 132 (1995)) (FIG. 7). The linking is effected using enzymes which are known to the skilled person and which are commercially available.

b) Construction of a plasmid which contains the chimeric promoter IL-2-CDE-CHR-Inr in the central component of the active compound The described chimeric IL-2 repressor module transcription unit is linked, at its 3' ends, to the 5' terminus of a DNA which contains the complete coding region of IL-10 (position ≦76 to ≧612, Moore et al., Science 248, 1230 (1990)) (FIG. 7). This DNA also contains a signal sequence which is required for secretion. Transcription control units and the DNA for IL-10 are cloned into PUC19/19 or Bluescript-derived plasmid vectors, which can be used, directly or in colloidal dispersion systems, for in-vivo administration. Alternatively, the chimeric genes can be transferred into viral vectors, or other suitable vectors, and injected.

c) Construction of a plasmid which contains two genes for active substances

The human IL-1 receptor promoter (pos. ≧-489 to ≧-1, Ye et al., PNAS USA 90, 229 (1993)) is linked, at its 3' end, to the 5' terminus of the CDE-CHR-Inr module of the human cdc25C gene (pos. -20 to +121 (Lucibello et al., EMBO J. 14, 132 (1995)) (see FIG. 7). The linking is effected using enzymes which are known to the person skilled in the art and which are commercially available.

The chimeric IL-1 receptor repressor module transcription control unit, which is prepared in this way, is linked, at its 3' end, to the 5' terminus of a DNA which contains the complete coding region of IL-10 (see FIG. 7). This DNA also contains the signal sequence which is required for secretion.

The 3' end of the DNA for IL-10 is now linked to the 5' end of the cDNA of the internal ribosome entry site (position ≦140 to ≧630; Pelletier and Sonnenberg, Nature 334, 320 (1988)), and their 3' end is subsequently linked to the 5' end of the DNA for the signal sequence of immunoglobulin (position ≦63 to >107, Riechmann et al., Nature 332, 323 (1988)). The 5' of the DNA for β-glucuronidase is linked to their 3' end (position ≦93 to ≧-1982, cDNA sequence without signal sequence, Oshima et al., PNAS USA 84, 685 (1985)). This active compound, which has thus been prepared, is then cloned into puc18/19 or into Bluescript-derived plasmid vectors, which can be used, directly or in colloidal dispersion systems, for in-vivo administration. Alternatively, the chimeric genes can be transferred into viral vectors or other suitable vectors, and injected.

7) Active Compound for Treating Arthritis 7.1. Choice of the activator sequence for arthritis An activator sequence is to be understood to be a nucleotide sequence (promoter or enhancer sequence) with which transcription factors interact which are formed or are active in synovial cells and inflammatory cells. Within the meaning of this invention, the preferred activator sequences include gene-regulatory sequences or elements from genes which encode proteins which are particularly expressed in synovial cells and inflammatory cells. Examples of these proteins are:

metalloproteinases (MMP) (collagenases, gelatinases and stromelysin) in particular
  MMP-1 (interstitial collagenase) (Lewis et al., Int. J. Immunopharm. 14, 497 (1992))
  MMP-2 (72 kD gelatinase) (Okada et al., Eur. J. Biochem. 194, 721 (1990))
  MMP-3 (stromelysin) (Saus et al., J. Biol. Chem. 263, 6742 (1988), Tetlow et al., Rheum. Internat. 13, 53 (1993))
  MMP-9 (92 kD golatinase) (Tetlow et al., Rheum. Internat. 13, 53 (1993))

Promoter sequences for the metalloproteinases have, for example, been published as follows:
  MMP-1 (interstitial collagenase) (Angel et al., Mol. Cell. Biol. 7, 2256 (1987)
  MMP-3 (stromelysin/transin) (Matrisian et al., Mol. Cell. Biol. 6, 1679 (1986), Kerr et al., Cell 61, 267 (1999)

tissue inhibitors of metalloproteinases (TIMP) in particular
  TIMP-1 (Kolkenbrock et al., Eur. J. Biochem. 198, 775 (1991), Faucher et al., Path. Biol. 37, 199 (1989))
  TINP-2 (Kolkenbrock et al., Eur. J. Biochem. 198, 775 (1991))
  TIMP-3 (Wick et al., J. Biol. Chemistry 269, 18953 (1994)).

The promoter sequences for TIMPs have been published as follows:
  TIMP-1 (Stearns et al., Proc. Annu. Meet. Am. Assoc. Cancer Res. 33, A131 (1992))
  TIMP-2 (De Clerck et al., Gene 139, 185 (1994))
  TIMP-3:

The invention furthermore relates to the promoter sequence, encompassing 500 base pairs, for the TIMP-3 gene described by Wick et al. (J. Biol. Chemistry 269, 18953 (1994)). This promoter sequence is composed, inter alia, of the binding sites for the transcription factors NF-1 (Mcisterernst et al., Nucl. Acids Res. 16, 4419 (1988), Santoro et al., Nature 334, 218 (1988)), Spl (Kadonaga et al., TIBS 11, 10 (1986)) and C/EBP (Cao et al., Genes Dev. 5, 1538 (1991), Landschulz et al., Science 243, 1681 (1989) and flanks the transcribed TIMP-3 gene sequence at the 5' end.

7.1.1. Characterization of the human TIMP-3 promoter sequence a) Isolation and sequence analysis of the 5α-flanking promoter sequence of the human TIMP-3 gene Induction of TIMP-3-mRNA expression during the $G_0 \rightarrow S$ progression is mainly due to activation of transcription of the TIMP-3 gene (Wick et al., J. Biol. Chem. 269, 18963 (1994)). The 5'-flanking sequence of the human TIMP-3 gene was cloned and the start point for transcription of the TIMP-3-mRNA was determined; the adjoining promoter region was then subjected to a structure/functional analysis. These investigations were intended to clarify the regulatory mechanisms underlying specific TIMP-3 expression during the $G_0 \rightarrow S$ and $G_1 \rightarrow S$ progression.

By means of genomic Southern Blot analysis, it was initially determined whether TINP-3 constitutes a single gene in the human genome or whether there exist several loci for the TIMP-3 gene or, possibly, TIMP-3 pseudogenes as well. For this purpose, genomic DNA was isolated from WI-38 cells, treated with the restriction endonucleases EcoRI, PstI and HindIII, and subjected to a Southern Blot analysis. A 690 bp 3'-TIMP-3 cDNA fragment was employed as the radioactively labeled probe. Since the probe only recognized one specific DNA fragment in every case, it is to be assumed that there is only one single TIMP-3 gene in the human genome.

In order to isolate the 5'-flanking TIMP-3 gene sequence, approx. $7 \times 10^5$ phage from a genomic WI-38 gene library were hybridized with a 300 bp 5'-TIMP-3 cDNA fragment. Of the thirteen recombinant phage clones which were isolated after this preliminary screening, four were also recognized by a 30 bp oligonucleotide from the 5' end region of the TIMP-3 cDNA. Since these phage probably also contained the 5' sequence region flanking the ATG start codon, one of the phage clones was selected for more detailed characterization and analysis. By means of a combined treatment with various restriction endonucleases and subsequent Southern Blot analysis, it was determined that the 13 kb genomic DNA insert in this phage clone contained approx. 4.7 kb of the 5'-flanking TIMP-3 gene sequence.

Figure 8:
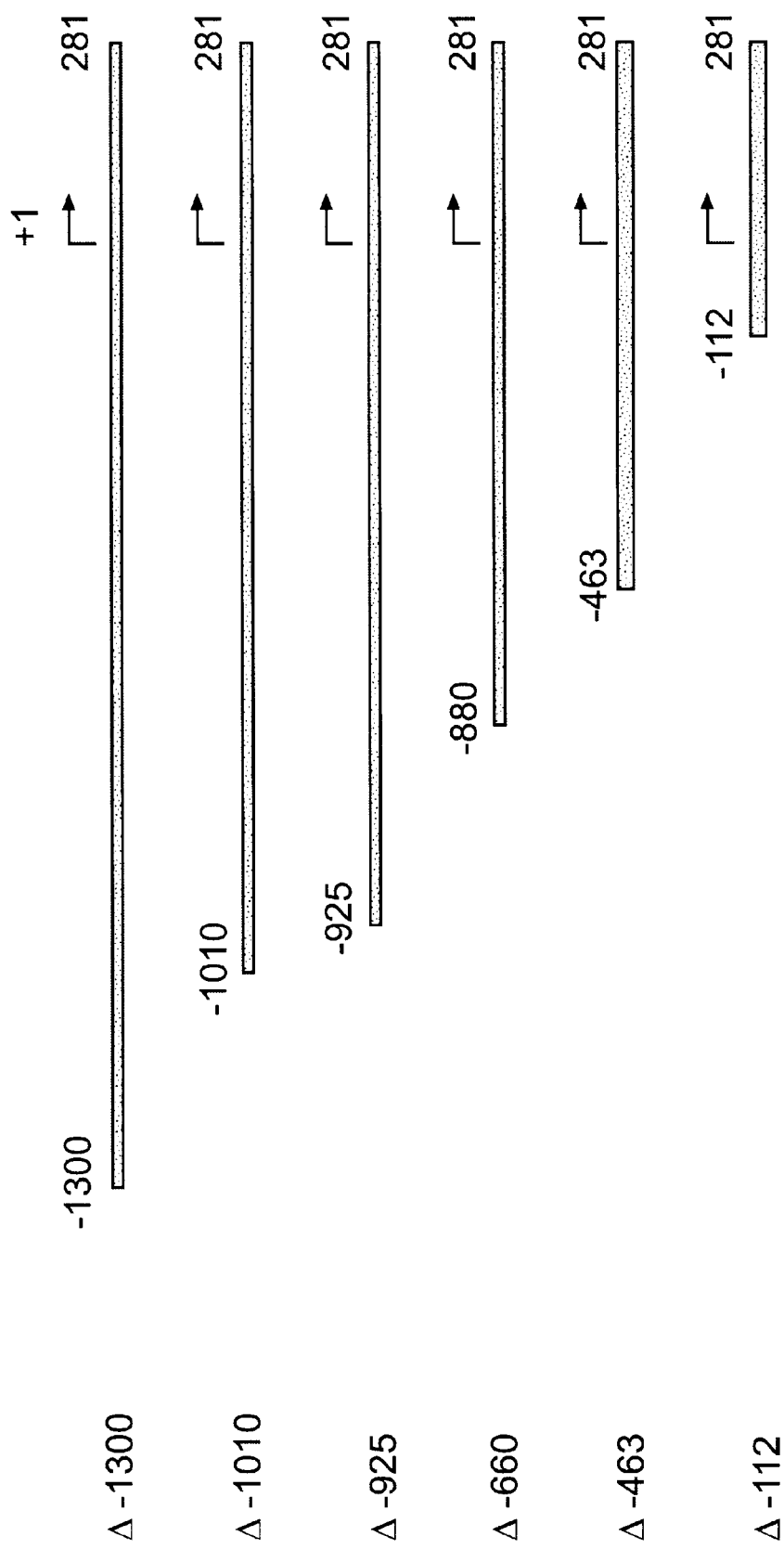

The nucleotide sequence of approximately 1500 bp of the 5'-flanking gene region was determined by analyzing the sequences of both strands. The 5' truncations of the cloned 5' gene region which were prepared for this purpose by means of exonuclease III treatment are illustrated in FIG. 8. The sequence region which, as a result of the structure/function analyses which are described below, turned out to be particularly important for the function of the TIMP-3 promoter is shown in FIG. 9 (SEQ ID NO:8). Computer-assisted analysis was used to identify a series of elements in the TIMP-3 promoter sequence which resemble the binding sites of the known transcription factors, inter alia 4 Sp1 binding sites, a possible NF-1 binding site and a C/EBP binding site (labeled in FIG. 9, SEQ ID NO:8).

b) Mapping the transcription start point of the TIMP-3 mRNA

In order to ascertain the start point(s) of transcription initiation, the 5' end of the TIMP-3 mRNA was determined by means of primer extension analysis. In this context, a transcription start site (nucleotide sequence: GGGCGGGCCCAACAGCCCG) (SEQ ID NO:9) was identified which is located 364 bp 5' of the ATG start codon (labeled in FIG. 9, SEQ ID NO:8). Despite careful examination of the nucleotide sequence situated upstream of the start site, neither a TATA box nor TATA-like sequences were found.

c) Investigations on the activity of the TIMP-3 promoter sequence

In order to determine the activity of the TIMP-3 promoter sequence in normally proliferating, resting and serum-stimulating cells, and to obtain the first leads with regard to functionally important promoter regions, the 5'-truncated promoter fragments which were used for the sequencing (see FIG. 8) were cloned into the promoterless pXP-2 vector (Nordeen, Biotechniques 6, 454 (1988)) upstream of the luciferase gene. Owing to its extremely low basal activity, this "reporter construct" is particularly suitable for carrying out transient expression analyses.

d) Activity of the TIMP-3 promoter sequence in normally proliferating and serum-stimulated NIH3T3 cells In order to demonstrate that the isolated TIMP-3 promoter sequence is active in transient expression analyses, i.e. can regulate transcription of the luciferase reporter gene, the TIMP-3 promoter deletion construct Δ–1010 (encompasses nucleotides –1010 to +281, see FIG. 8) was transfected into NIH3T3 cells and the luciferase activity was determined in these normally proliferating or serum-stimulated transfected cells. For comparison, the expression was also ascertained of further luciferase/promoter constructs which contained the herpes virus tk promoter (pT81 Lucibello and müller, meth. Mol. Cell Biol. 1, 9 (1989)), a 5×TRE minimum promoter (Angel et al., Mol. Cell Biol. 7, 2256 (1987)), an RSV LTR (Setoyama at al., Proc. Natl. Acad. Sci. USA 83, 3213 (1986) or a 937 bp fragment of the human cyclin D1 promoter (Herber et al., Oncogene 9, 1295 (1994)). The results of these investigations are presented in Table 2.

In normally proliferating NIH3T3 cells (Tab. 2A), expression of the TIMP-3 promoter construct Δ–1010 was approx. 3-fold higher than that of the 5×TRE minimum promoter and 7-fold higher than that of the cyclin D1 promoter construct. The RSV-LTR reporter plasmid alone exhibited an activity which was approx. 2-fold higher than that of the TIMP-3 promoter construct. These results indicate that the transcriptional activity of the human TIMP-3 promoter is comparatively high. As shown in Tab. 2B and FIG. 11, the TIMP-3 promoter construct Δ–1010 was also markedly induced in cells which had been stimulated with 20% FCS for 4 h following two days of serum withdrawal. In this case, expression increased approx. 7 to 8-fold as compared with resting ($G_0$) cells, which was approximately 3.5-fold and 2.4-fold, respectively, higher than the induction values which were observed for the 5×TRE reporter construct and the cyclin D1 promoter construct. By contrast, expression of the herpes simplex tk promoter luciferase construct (pT81) was not induced following serum stimulation.

Figure 10:
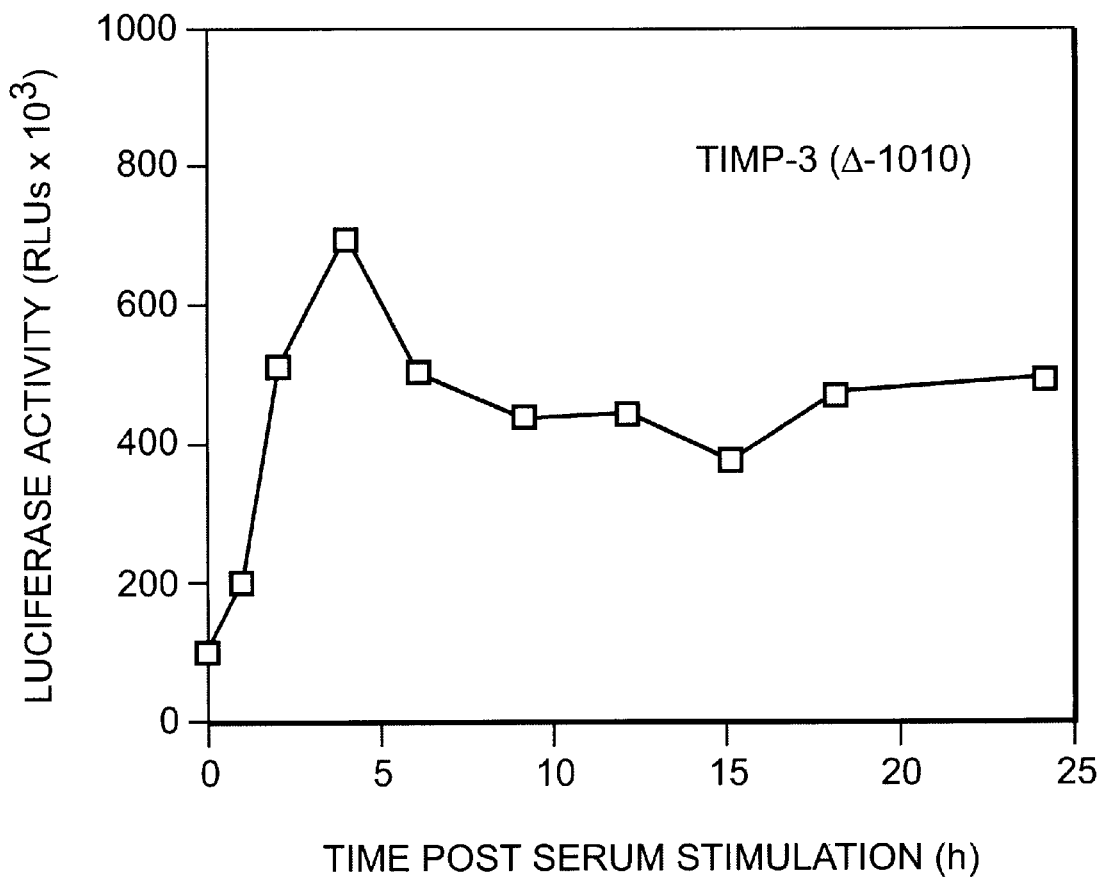

FIG. 10 depicts the kinetics of the induction of the Δ–1010 TIMP-3 promoter construct following stimulation of resting cells with serum. The luciferase activity increased after 1 h and reached maximum values, with a 7-fold induction, after 4 h.

In summary, these results demonstrate that the Δ–1010 TIMP-3 promoter construct which was used possesses, if not all, at least the essential regulatory elements which are required for efficient transcription and for inducibility by serum.

e) Structural and functional analysis of the TIMP-3 promoter sequence

The intention was that a structural and functional analysis of the isolated TIMP-3 promoter sequence would provide the first indications of those promoter regions which were functionally important for basal expression and for serum inducibility. For this, the activities of the different TIMP-3 promoter deletion constructs (see FIG. 8), which were prepared for the promoter sequencing and subcloned into the pXP-2 vector, were determined in transient expression analyses. Analysis of the basal expression of the different deletion constructs in normally proliferating NIH3T3 cells (FIG. 11) produced three important results:

1. The promoter construct Δ–1010 exhibited the strongest expression. Truncating this construct by further 85 bp (construct Δ–925) resulted in an almost 2-fold decline in the activity of the promoter. This points to the presence in the region between positions –1010 and –925 of one or more elements which are involved in transcription activation.
2. The activity of the promoter was not significantly affected by further truncations of the 5' end up to position –112. The region between –925 and –112 probably does not, therefore, contain any sequence regions which are important for the activity of the promoter.
3. By contrast, the region between positions –1300 and –1010 appears to exert a negative effect on the activity of the promoter, as is evident from the fact that the expression of the Δ–1300 deletion construct was approx. 4-fold less than that of the Δ–1010 promoter construct.

In the concluding experiment, the serum inducibility of the different TIMP-3 promoter deletion constructs was analyzed. The results of these expression analyses, which were carried out as described in Table 2, are depicted in FIG. 11b. The similarity of the expression profile between normally proliferating (FIG. 11a), resting and serum-stimulated cells (FIG. 11b) is striking. However, the expression values in resting cells were approx. 2-fold lower than those in proliferating cells and were induced 2.9-fold to 8.5-fold at 4 h after serum stimulation. While, as shown in the proliferating cells (FIG. 11a), the region between positions Δ–1300 and Δ–1010 exerts a negative effect on the activity of the promoter in resting and serum-stimulated cells, it has no influence on the serum inducibility of construct Δ–1300 (8.5-fold induction). In this case too, the highest luciferase activities were once again measured using the –1010 deletion construct.

Further truncations of the 5' end up to position –660 only resulted in a 1.5-fold to 2-fold decline in the activity of the promoter. However, all these constructs (Δ–1300, Δ–1010, Δ–925, Δ–660) exhibited a marked, 6-fold to 8-fold induction following the addition of serum. While truncation by a further 200 bp up to position –463 (Δ–463) resulted in a further 2-fold decline in activity, it likewise had no effect on the serum inducibility of the construct. It was only construct Δ–112 which, with only a 3-fold increase in expression following serum stimulation, exhibited a 50–65% reduction in its serum inducibility. This indicates that the region between positions –463 and –112 contains (an) element(s) which is/are of importance for the serum inducibility of the TIMP-3 promoter. Additional regions between positions –463 and –660 and also –925 and –1010 amplify the serum-induced activity of the promoter in a general and cell cycle-independent manner.

The results of the characterization and the structural and functional analysis of the 5'-flanking TIMP-3 gene region can be summarized as follows:

TIMP-3 is a gene which does not possess a TAT box. Nevertheless, transcription is initiated at only one start site 364 bp upstream of the ATG start codon. Compared with other promoters, the TIMP-3 promoter sequence has a relatively high activity, for which the first 112 bp are adequate. Numerous Sp1-binding sites are located in this region. In addition, the activity of the promoter exhibits marked induction following serum stimulation of resting cells, the kinetics of which induction corresponds to the expression of TIMP-3 mRNA during the $G_0$–S progression. The regulatory elements which are responsible for the serum inducibility are located in the region between positions –112 and –463.

Promoters for the

GM-CSF receptor (Nakagawa et al., J. Biol. Chem. 269, 10905 (1994))

macrophage colony stimulating factor (N-CSF) receptor
(Yue et al., Mol. Cell. Biol. 13, 3191 (1993), Zhang et al., Mol. Cell. Biol. 14, 373 (1994))

Type I and type II macrophage scavenger receptors
(Mouton et al., Mol. Cell. Biol.14, 4408 (1994))

are also activator sequences within the meaning of this invention.

7.2. Choice of the active substance for arthritis

Within the meaning of the invention, an active substance is to be understood as being a DNA sequence whose expressed protein directly or indirectly inhibits inflammation, for example in a joint, and/or promotes the reconstitution of extracellular matrix (cartilage and connective tissue) in a joint. The following proteins, for example, are proteins of this nature (the DNA sequence for each particular protein can be obtained from the literature references which are cited):

IL-1 receptor antagonist (IL-1 RA)
(Thompson et al. (1992), Eisenberg et al., Nature 343, 341 (1990), Carter et al., Nature 344, 63 (1990))
IL-1 RA inhibits the binding of IL-1 and β to the specific receptor (Conti et al., (1992), Granowietz et al., (1992)), IL-1 activates synovial cells and thereby promotes inflammation (Dayer et al., Eur. Cytokine Network 5/6, 563 (1994))

soluble IL-1 receptor
(Sims et al., Clin. Immun. Immunopath. 72, 9 (1994), Sims et al., Nature 35, 88 (1988), Sims et al., PNAS USA 86, 8946 (1989) (I), Dower et al., J. Exp. Med. 162, 501 (1985), Chizzonite et al., PNAS 86, 8029 (1989), McMahan et al., EMBO J. 10, 2821 (1991) (II), Sims et al., Science 241, 585 (1988)) Soluble IL-1 receptor binds and inactivates IL-1 (Fanslow et al., Science 248, 739 (1990), Jacobs et al., J. Immunol. 146, 2983 (1991))

IL-6
(Hirano, Int. J. Cell Cloning 9, 166 (1991), Brach et al., Int. J. Clin Lab. Rec. 22, 143 (1992), Wong et al., Immunol. Today 9, 137 (1988), Brakenhoff et al., J. Immunol. 143, 1175 (1989), Yasukawa et al., EMBO J. 6, 2939 (1987)) IL-6 increases the secretion of TIMP and superoxides and diminishes the secretion of IL-1 and TNF by synovial cells and chondrocytes (Shingu et al., Clin. Exp. Immunol. 94, 145 (1993), Shingu et al., Inflammation 18, 613 (1994)).

soluble TNF receptor
(Olson et al., Eur. Cytokine Network 4, 169 (1993), Tartaglia et al., Immunol. Today 13, 151 (1992), Nophar et al., EMBO J. 9, 3269 (1990), Himmler et al., DNA Cell Biol. 9, 705 (1990), Aggarwal et al., Nature 318, 665 (1985), Gray et al., PNAS 87, 7380 (1990), Tartaglia et al., Immunol Today 13, 151 (1992), Loetcher et al., Cell 61, 351 (1990), Schall et al., Cell 61, 361 (1990), Smith et al., Science 248, 1019 (1990), Goodwin et al., Mol. Cell. Biol. 11, 3020 (1991))
Soluble TNF receptor binds and inactivates TNF. TNF activates synovial cells to increase their secretion of metalloproteinases (Dayer et al., Eur. Cytokine Network 5/6, 563, 1994))

IL-4
(Paul, J. Am. Soc. Hemat. 77, 1859 (1991), Yokota et al., PNAS USA 83, 5894 (1986), Paul, Blood 77, 1859 (1991), von Leuven et al., Blood 73, 1142 (1989), Arai et al., J. Immunol. 142, 274 (1989))
IL-4 inhibits the formation and secretion of IL-1, TNF and MMP (Corcoran et al., J. Biol. Chemistry 267, 515 (1992), Dayer et al., Eur. Cytokine Network 5/6, 563 (1994), to Velde et al., Blood 76, 1392 (1990))

IL-10
(Moore et al., Science 248, 1230 (1990), Vieira et al., PNAS USA 88, 1172 (1991), Kim et al., J. Immunol. 148, 3618 (1992))
IL-10 inhibits the formation and secretion of IL-1, TNFα and MMP and increases the secretion of TIMP (Dayer et al., Eur. Cytokine Network 5/6, 563 (1994))

insulin-like growth factor (IGF-1)
(Jansen et al., Nature 306, 609 (1983), Ullrich et al., EMBO J. 3, 361 (1984), Bell et al., PNAS 82, 6450 (1985), Rotwein et al., PNAS 83, 77 (1986), J. Biol. Chem. 261, 4828 (1986), Jansen et al., FEBS Lett. 179, 243 (1985)), Tobin et al., Mol. Endocrin. 4, 1914 (1990), Macaulay, Brit. J. Cancer 65, 311 (1992))
IGF-1 stimulates the synthesis of extracellular matrix.

TGFβ
in particular
TGFβ1 and TGFβ2
(Massague, Ann. Rev. Cell. Biol. 6, 597 (1990), Kondiah et al., J. Biol. Chem. 265, 1089 (1990), Garnier et al., J. Molec. Biol. 120, 97 (1978), Wahl et al., Immunol. Today 10, 258 (1989), Dupuy D'Angeac et al., J. Cell Physiol. 147, 460 (1991))
TGFβ stimulates the synthesis of extracellular matrix.

superoxide dismutase (Folz et al., Genomics 22, 162 (1994), Wan et al. 13/11, 1127 (1994))

TIMP (tissue inhibitors of metalloproteinases)
in particular
TIMP-1 (Docherty et al., Nature 318, 66 (1985))
TIMP-2 (Stetler-Stevenson et al., J. Biol. Chem. 265, 13933 (1990))
TIMP-3 (Wick et al., J. Biol. Chemistry, 269, 18953 (1994))

However, within the meaning of the invention, DNA sequences of fusion proteins formed between the listed cytokines and growth factors, or the extracellular moiety of the receptors, on the one hand, and the Fc moiety of human immunoglobulin, on the other hand, can also be used as the active substance. cDNA sequences of this nature, and their preparation, have been described in EPA 0464 633 A1.

7.3. Combination of identical or different active substances for arthritis

The invention additionally relates to an active compound in which a combination of the DNA sequences of several identical antiinflammatory substances (A,A) or different antiinflammatory substances (A,B) is present. The cDNA of an internal ribosome entry site (IRES) is preferably intercalated, as a regulatory element, for expressing two DNA sequences.

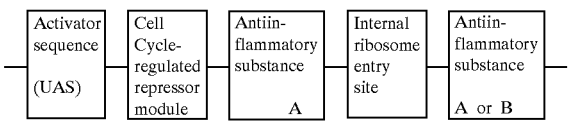

IRESs of this nature have, for example, been described by Mountford and Smith TIG 11, 179 (1995), Kaufman et al., Nucl. Acids, Res. 19, 4485 (1991), Morgan et al., Nucl. Acids Res. 20, 1293 (1992), Dirks et al., Gone 128, 247 (1993), Pelletier and Sonenberg, Nature 334, 320 (1988) and Sugitomo et al., BioTechn. 12, 694 (1994).

Thus, the cDNA of the IRES sequence of poliovirus (position ≦140 to ≧630 of the 5' UTR (Pelletier and Sonenberg, Nature 334, 320 (1988)) can be used to link the DNA of antiinflammatory substance A (at the 3' end) to the DNA of antiinflammatory substance B (at the 5' terminus).

Depending on the combination employed, an active compound of this nature exhibits either an additive (A+A, A+$B_1$) or a synergistic effect within the meaning of the invention.

7.4. Choice of the ligand for arthritis

Substances which bind to the surface of synovial cells are preferred as ligands for viral and nonviral vectors, for example in polylysine/ligand conjugates. These substances include monoclonal or polyclonal antibodies or antibody fragments which bind, by their variable domains, to membrane structures of synovial cells or inflammatory cells, examples of which structures are

- vimentin (Miettinen et al., Am. J. Pathol. 117, 18 (1984))
- fibronectin (Wojciak et al., clin. exp. Immunol. 93, 108 (1993))

These substances also include monoclonal or polyclonal antibodies or antibody fragments which bind, by their constant domains, to Fc receptors (Rojanasakul et al., Pharm. Res. 11, 1731 (1994)).

The murine monoclonal antibodies should preferably be employed in humanized form. The humanization is effected in the manner described by Winter et al. (Nature 349, 293 (1991)) and Hoogenbooms et al. (Rev. Tr. Transfus. Hemobiol. 36, 19 (1993)). Antibody fragments are prepared in accordance with the state of the art, for example in the manner described by Winter et al., Nature 349, 293 (1991), Hoogenboom et al., Rev. Tr. Transfus. Hemobiol. 36, 19 (1993), Girol, Mol. Immunol. 28, 1379 (1991) or Huston et al., Int. Rev. Immunol. 10, 195 (1993).

In addition, the substances also include all active compounds which bind to membrane structures or membrane receptors on synovial cells. For example, they include cytokines or growth factors, or their fragments or constituent sequences thereof, which bind to receptors which are expressed by synovial cells, for example IL-1-RA, TNFα, IL-4, IL-6, IL-10, IGF and TGFβ.

In addition, these substances include ligands whose essential constituent is terminally located mose, which binds to mannose-6-phosphate receptors on macrophages (Perales et al., Eur. J. Biochem. 226, 255 (1994)).

7.5. Preparation of the active compound for arthritis a) Construction of the chimeric promoter TIMP-3-CDE-CHR-Inr The human TIMP-3 promoter (pos. ≦−463 to ≧−2), or truncated variants (pos. ≦−112 to ≧−2 or ≦−463 to ≧−10 or ≦−112 to ≧−10), is/are linked, at its/their 3' end, to the 5' terminus of the CDE-CKR-Inr module (pos. ≦−20 to ≧+121) of the human cdc25C gene (pos. ≦−20 to ≧+121) (FIG. 12). The linking is effected using enzymes which are known to the skilled person and which are commercially available. Different fragments of the TIMP-3 promoter sequence are used in order (1) to be able to employ a promoter fragment which is as short as possible (while retaining as efficient a transcription as possible) and (2) to eliminate undesirable effects of the TIMP-3 initiator (region around +1) on regulation by CDE/CHR.

b) Construction of a plasmid which contains the central component of the active compound The chimeric TIMP-3 promoter module transcription control units described in a) are linked, at their 3' ends, to the 5' terminus of a DNA which contains the complete coding region, of 152 amino acids in length, of the IL-1 receptor antagonist (DNA, pos. ≦25 to ≧557; Eisenberg et al., Nature 343, 341 (1990)). This DNA also contains the signal sequence (25 N-terminal amino acids) which is necessary for secretion (FIG. 12). Transcription control units and IL-1 receptor antagonist DNA are cloned into pUC18/19 or Bluescript-derived plasmid vectors which can be used, either directly (Yovandich et al., Hum. Gene Ther. 6, 603 (1995)) or in colloidal dispersion systems, for in-vivo administration for transducing synovial cells. Alternatively, the transcription control units and IL-1 receptor antagonist DNA, which have been joined together, can be transferred into viral vectors, or other suitable vectors, and injected.

8) Preparation of an Active Compound Against Infectious Agents

The active compound can be prepared in two basically different forms:

- for the therapy of virus infections and invasions of parasites, or else
- for the prophylaxis of infectious diseases caused by viruses, bacteria or parasites.

Vaccines are used for the prophylaxis of infectious diseases. However, the possibilities of preparing effective vaccines in a conventional manner are limited (Brown, Int. J. Technol. Assessm. Health Care 10, 161 (1994), Ellis Adv. Exp. Ned. Biol. 327, 263 (1992), Arnon et al., FASEB J. 6, 3265 (1992)).

The technology of DNA vaccines was developed as a consequence. However, these DNA vaccines raise questions with regard to safety and side effects (Fynan et al., Int. J. T Immunopharm. 17, 79 (1995), Donnelly et al., Immunol. 2, 20 (1994)).

Active compounds for the prophylaxis of infectious diseases within the meaning of this invention are characterized by a high degree of safety on account of their cell specificity and their regulation by the cell cycle.

8.1. Choice of the activator sequence a) Regarding the therapy of infectious diseases Promoter sequences of proteins which are formed, in particular, by bacteria or parasites, or else promoter sequences which are derived from those viruses which transform the cells which they have infected and stimulate them to proliferate, should be selected as activator sequences.

These viruses include, for example, HBV, HCV, HSV, HPV, RIV, EBV and HTLV.

Promoter sequences for these viruses have been described as follows:

HBV (Sato et al., Annals Int. Med. 122, 241 (1995), Raney et al., J. Gen. Virol. 75, 2671 (1994), Raney et al., J. Virol. 66, 6912 (1992), Zhang et al., J. Virol. 67, 1472 (1993), Guo et al., J. Virol. 65, 6686 (1991))

HCV (Matsuura et al., Intervirol. 37, 114 (1994), Kumar et al., J. General Virol. 73, 1521 (1992), Kim et al., Jap. J. Med. Sci. Biol. 47, 211 (1994))

HSV (Greco et al., J. Gen. Virol. 75, 1693 (1994), Papavassiliou et al., J. Biol. Chem. 265, 9402 (1990))

HPV (May et al., EMBO J. 13, 1460 (1994), Thierry et al., EMBO J. 6, 3391 (1987))

EBV (Chen et al., DNA and Cell Biol. 14, 205 (1995), Nonkwelo et al., Virol. 206, 183 (1995), Smith et al., J. Virol. 66, 706 (1992), Lear et al., J. Virol. 66, 7461 (1992), Rooney et al., J. Virol. 66, 496 (1992))

HTLV
(Ohtani et al., EMBO J. 6, 389 (1987))
HIV
(Koken et al., Virol. 191, 968 (1992), Berghout et al., J. Virol. 66, 139 (1992), Cherrington et al., EMBO J. 11, 1513 (1992), Rosen et al., Cell 41, 813 (1985))

The HIV LTR (long terminal repeat) sequence serves as the binding site for cellular transactivating factors which are found in many different cells and tissues (Levy, AIDS 4, 1051 (1990)). These factors include the transcription factors SP1, EBP-1, UBP-1, NF-KB, LBP-1 and CTN-NF (Garcia et al., EMBO J. 6, 3761 (1987)). The transactivator region (TAR), to which the HIV transactivator protein (TAT) binds, is located at the 3' end of the LTR (Cullen, Cell 63, 655 (1986), Selby et al., Genes and Dev. 3, 547 (1989)). Another binding site for the TAT protein has been described in the NF-KB domain of the HRIV-LTR (Taylor et al., EMBO J. 11, 3395 (1992)). The HIV transactivator protein (TAT) can increase expression of the HIV LTR gene more than a hundred-fold (Dayton et al., Cell 44, 941 (1986), Rosen et al., Nature 319, 555 (1986), Laspia et al., Cell 59, 283 (1989)). Consequently, the TAR region is an integral component of the transcription and translation of HIV-LTR (Garcia et al., EMBO J. 8, 765 (1989)). HIV-LTR can be used as a promoter not only for HIV genes but also for heterologous reporter genes and, in the latter case, also without the presence of HIV-TAT (Banerjee et al., Hepatol. 10, 1008 (1989), Virology 179, 410 (1990)). There are grounds for believing that this promoter activity is activated by cellular transcription factors which functionally resemble HIV-TAT. However, this activation by cellular TAT-like factors is generally less than that by HIV-TAT (Sodroski et al., Science 229, 74 (1985), Dayton et al., Cell 44, 941 (1986), Rosen et al., Nature 319, 555 (1986)). Nevertheless, a relatively strong activation of the HIV-LTR by cellular TAT-like factors has been observed in liver cells (Pizzela and Banerjee, DNA and Cell Biol. 13, 67 (1994)).

TAR is present both as DNA and as RNA. However, experimental studies show that the TAR binds, as RNA, to TAT, by means of the secondary structure of this RNA, and is functionally active (Roy et al., J. Virol. 64, 1402 (1990)), i.e. binds to the corresponding promoter DNA and activates this DNA (Berkhout et al., Cell 62, 757 (1990)). TAR is only active to a trivial extent, if at all, in combination with a heterologous promoter (Maesing et al., Cell 48, 691 (1987), Berkhout et al., Cell 62, 757 (1990)); in addition, optimum functioning of TAR is only ensured in direct proximity to the nucleotide sequences of the HIV-LTR promoter which are adjacent to the 5' terminus of TAR, in particular the NF-KB/SP1-binding region (Berkhout et al., Cell 62, 757 (1990)).

Consequently, in the case of HIV, the entire LTR sequence, including the TAR sequence (position $\leq$−453 to $\geq$+80, Rosen et al., Cell 41, 813 (1985)) should be employed as a virus-specific promoter.

c) Regarding the prophylaxis of infectious diseases

Promoter sequences of the genes of those proteins which are formed in particularly large quantity in activated macrophages and activated lymphocytes should be selected as activator sequences. Examples of proteins of this nature, and their genes, were listed in Section 6.1.

8.2. Choice of the active substance a) Regarding the therapy of infectious diseases The DNA of a protein which exhibits cytostatic, cytotoxic and antiviral effects should be selected as the active substance. Examples of cytotoxic or cytostatic proteins have already been listed in Section 6.2.e-g). When an enzyme is chosen (see Section 6.2.g in this regard), a compound subsequently has to be administered which can be cleaved by this enzyme and which is the precursor of an antiviral, cytotoxic or antiparasitic substance.

Within the meaning of this invention, antivirally active cytokines and growth factors are also active substances for antiviral proteins. They include, for example, the DNA sequences for the following active substances:

IFNα

(Henco et al., J. Mol. Biol. 185, 227 (1985), Pestka et al., Ann. Rev. Biochem. 56, 727 (1987), Weissmann et al., Phil. Trans. R. Soc. Lond. B299, 7 (1982), Goeddel et al., Nature 290, 20 (1981))

IFNβ

(Sen et al., J. Biol. Chem. 267 5017 (1992), Mark et al., EP 192 811, EP 234 599, US 45 88 585)

IFN-γ

(Gray et al., Nature 295, 503 (1982), Yip et al., PNAS USA 79, 1820 (1982), Rinderknecht et al., J. Biol. Chem. 259, 6790 (1984))

TNFβ

(Gray et al., Nature 312, 721 (1984), Li et al., J. Immunol. 138, 4496 (1987), Aggarwal et al., J. Biol. Chem. 260, 2334 (1985))

TNFα

(Beutler et al., Nature 320, 584 (1986), Kriegler et al., Cell 53, 45 (1988)

IL-1

(Furntani et al., Nucl. Acids Res. 14, 3167 (1986), Lafage et al., Blood 73, 104 (1989), March et al., Nature 315, 641 (1985), Bensi et al., Gene 52, 95 (1987), Auron et al., PNAS 81, 7907 (1984), Clark et al., Nucl. Acids Res. 14, 7897 (1986))

TGFβ

(Massague Ann, Rev. Cell. Biol. 6, 597 (1990), Kondiah et al., J. Biol. Chem. 265, 1089 (1990), Garnier et al., J. Molec. Biol. 120, 97 (1978))

However, within the meaning of the invention, DNA sequences of fusion proteins formed between the listed cytokines and growth factors, or the extracellular moiety of the receptors, on the one hand, and the Fc moiety of human immunoglobulin, on the other hand, can also be used as active substances. DNA sequences of this nature, and their preparation, have been described in EP 0 464 633 A1.

In addition, the DNA sequence for an antibody having a specificity which inactivates the particular virus, or its $V_H$ and $V_L$-containing fragments, or its $V_H$ and $V_L$ fragments which are connected via a linker, prepared, for example, in accordance with the methodology described by Marasco et al. (Proc. Natl. Acad. Sci. USA 90, 7889 (1993)), is also an active substance within the meaning of this invention. Examples of antibodies having such specificity against viruses are listed in Section 8.4.

In addition, the DNA sequence for a Rev-binding protein is an active substance within the meaning of this invention. These proteins bind to the Rev-RNA and inhibit Rev-dependent post-transcriptional steps in retrovirus gene expression. The following are examples of Rev-binding proteins:

RBP9-27

(Constantoulakis et al., Science 259, 1314 (1993), Reid et al., PNAS USA 86, 840 (1989))

RBP1-8U (Kerr and Stark, FEBS Lett. 285, 194 (1991), Friedman et al., Cell 38, 745 (1984))

RBP1-8D (Lewin et al., Eur. J. Biochem. 199, 417 (1991))
pseudogenes of RBP1-8
(Lewin et al., Eur. J. Biochem. 199, 417 (1991))
b) Regarding the prophylaxis of infectious diseases The DNA of a protein which is formed by the infectious pathogen and which leads, as the result of an immune reaction, i.e. by means of antibody binding and/or by means of cytotoxic T lymphocytes, to the neutralization and/or destruction of the pathogen, should be selected as the active substance. Neutralization antigens of this nature are already used as vaccination antigens (see review in Ellis, Adv. Exp. Ned. Biol. 327, 263 (1992)). Examples of DNA sequences which encode neutralization antigens can be obtained through the following papers:

influenza A virus antigen
(Ulmer et al., Science 259, 1745 (1993), Robinson et al., Vaccine 11, 957 (1993), Fynan et al., Int. J. Immunopharmac. 17, 79 (1995))

HIV antigens
(Wang et al., PNAS USA 90, 4156 (1993))

rabies virus antigen
(Donnelly et al., Immunol. 2/1, 20 (1994))

HSV (herpes simplex virus) antigen
(Fleckenstein et al., Nature 274, 57 (1978))

RSV (respiratory syncytial virus) antigen
(Du et al., Bio/Tech. 12, 813 (1994), Hall, Science 265, 1393 (1993))

parainfluenza virus antigen
(Du et al., Bio/Techn. 12, 813 (1994))

rotavirus antigen
(Albert et al., J. Clin. Microbiol. 25, 183 (1987), Anderson et al., J. Infect. Dis. 153, 823 (1986), Battaglia et al., J. Infect. Dis. 155, 140 (1987), Chanock et al., J. Infect. Dis. 148, 49 (1983), Dyall-Smith et al., J. Virol. 38, 1099 (1981), Glass et al., Science 265, 1389 (1994))

VZV (varicella zoster virus) antigen
(Straus et al., Ann. Intern. Ned. 109, 438 (1988), Gershon, Pediatr. Infect. Dis. 2, 171 (1991), Kinchington et al., J. Virol. 64, 4540 (1990))

CMV (cytomegalo virus) antigen
(Plotkin, Science 265, 1383 (1994))

measles virus antigen
(Katz and Kellin, Science 265, 1391 (1994))

HPV (human papilloma virus) antigen
(Tindl and Frazer, Curr. Topics Microbial. Immunol. 186, 217 (1994))

HBV (hepatitis B virus) antigen
(Valenzuela et al., Nature 280, 815 (1979), Heerman et al., J. Virol. 52, 396 (1984))

HCV (hepatitis C virus) antigen
(Cerny et al., Curr. Topics Microbiol. Immunol. 189, 169 (1994), Esteban et al., Prog. Liver Dis. 10, 253 (1992), Jung et al., Eur. J. Clin. Invest. 24, 641 (1994))

HDV (hepatitis D virus) antigen
(Iwarson, Scand. J. Infect. Dis. 24, 129 (1992), Consolo et al., Nephron. 61, 251 (1992))

HEV (hepatitis E virus) antigen
(Iwarson, Scand. J. Infect. Dis. 24, 129 (1992), Consolo et al., Nephron. 61, 251 (1992))

HAV (hepatitis A virus) antigen
(d'Hondt, Vaccine 10, 48 (1992), Andre, J. Infect. Din. 171, 33 (1995), Lemon et al., Vaccine 10, 40 (1992), Melnick et al., Vaccine 10, 24 (1992), Flehmig, Baillieres Clin. Gastroenterol. 4, 707 (1990))

Vibrio cholera antigen
(Levine and Kaper, Vaccine 11, 207 (1993))

Borrelia burgdorferi antigen
(Schaible et al., Immunol. Letters 36, 219 (1993), Wallich et al., Lab. Med. 17, 669 (1993))

Helicobacter pylori antigen
(Crabtree et al., Lancet 338, 332 (1991), Blazer, J. Infect. Dis. 161, 626 (1990), Cover and Blaser, J. Biol. Chem. 267, 10570 (1993), Cover et al., Infect. Immunol. 58, 603 (1990), Dunn et al., J. Biol. Chem. 265, 9464 (1990), Dunn et al., Infect. Immunol. 60, 1946 (1992), Lage et al., Acta Gastroenterol. Belg. 56, (suppl.), 61 (1993), Mobley et al., Scand. J. Gastroint. 26 (suppl. 187), 39 (1991))

malaria antigen
(Nussenzweig and Long, Science 265, 1381 (1994), Maurice, Science 267, 320 (1995), Enders et al., Vaccines 10, 920 (1992), Knapp et al., Infect. Imm. 60, 2397 (1992))

However, within the meaning of the invention, active substances of this nature also include the DNA of an antiidiotype antibody, or its antigen-binding fragments, whose antigen-binding structures constitute the complementary determining regions, copies of the protein structure or carbohydrate structure of the neutralization antigen of the infectious pathogen.

Antiidiotype antibodies of this nature can, in particular, replace carbohydrate antigens in the case of bacterial infectious pathogens.

Antiidiotypic antibodies of this nature, and their cleavage products, have been reviewed by Hawkins et al. (J. Immunother. 14, 273 (1993)) and Westerink and Apicella (Springer Seminars in Immunopathol. 15, 227 (1993))

8.3. Combination of identical or different active substances for the therapy or prohylaxis of infectious diseases The invention furthermore relates to an active compound in which a combination of the DNA sequences of identical active substances (A,A) or different active substances (A,B) is present. The cDNA of an internal ribosome entry site (IRES) is preferably intercalated, as a regulatory element, for expressing two sequences.

IRESs of this nature have been described, for example, by Montford and Smith (TIG 11, 179 (1995), Kaufman et al., Nucl. Acids Res. 19, 4485 (1991), Morgan et al., Nucl. Acids Res. 20, 1293 (1992), Dirks et al., Gene 128, 247 (1993), Pelletier and Sonenberg, Nature 334, 320 (1988) and Sugitomo et al., BioTechn. 12, 694 (1994).

Thus, the cDNA of the IRES sequence of poliovirus (position $\leq 140$ to $\geq 630$ of the 5' UTR (Pelletier and Sonenberg, Nature 334, 320 (1988)) can be used to link the DNA of viral substance A (at the 3' end) and the DNA of antiviral substance B (at the 5' terminus)

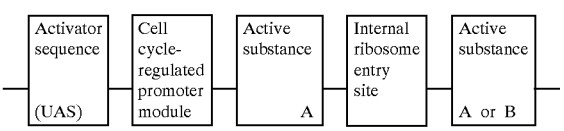

Depending on the combination, an active compound of this nature exhibits either an additive (A+A, A+B1) or synergistic effect within the meaning of the invention.

Thus, for example, two identical or two different antiviral active substances can be combined with each other for the therapy of virus diseases.

Several active substances, which encode different antigens of one infectious pathogen or of different infectious pathogens, can be combined with each other in the prophylaxis of infectious diseases. In addition, the active substance which encodes the antigen of an infectious pathogen can be combined with an active substance which encodes a cytokine or a cytokine receptor.

The cytokines or cytokine receptors, which are in this way formed concomitantly with the infectious pathogen antigen (after injecting the active compound), can influence the nature and strength of the developing immune reaction.

DNA sequences for cytokines and cytokine receptors which amplify the humoral immune reaction have already been described in 6.2.d), while those for amplifying the cellular immune reaction have been described in 6.2.a) and 6.2.c).

The following are examples of DNA sequences for cytokines which amplify the immune reaction as a whole:

IL-1α
   (Fenton, Int. J. Immunopharm. 14, 401 (1992), Furntani et al., Nucl. Acids Res. 14, 3167 (1986), Lafage et al., Blood 73, 104 (1989), March et al., Nature 315, 641 (1985))

IL-1β
   (Bensi et al., Gene 52, 95 (1987), Auron et al., PNAS 81, 7907 (1984), Clark et al., Nucl. Acids Res. 14, 7897 (1986))

IL-2
   (Fletscher et al., Lymphok. Res. 6, 45 (1987), Matsui et al., Lymphokines 12, 1 (1985), Tanaguchi et al., Nature 302, 305 (1983))

GM-CSF
   (Gough et al., Nature 309, 763 (1984), Nicola et al., J. Biol. Chem. 254, 5290 (1979), Wong et al., Science 228, 810 (1985))

8.4. Choice of the ligands for infectious pathogens

The ligands for the therapy of infectious diseases include antibodies or antibody fragments which are directed against the infectious pathogens. For example, in the case of viral infections, these are the viral antigens which are expressed on the cell membrane of virus-infected cells.

Antibodies of this nature have, for example, been described for cells infected with the following viruses:

HBV (Shonval et al., PNAS USA 79, 650 (1982), Intercell. Intracell. Comm. 2, 221 (1986), Klein et al., Virus Genes 5, 157 (1991))

HCV (Takahashi et al., Virol. 191, 431 (1992))

HSV (Sanchez-Pescador et al., J. Infect dis. 166, 623 (1992))

HPV (Doorbar et al., Virol. 187, 353 (1992))

HIV (Nishino et al., Vaccine 10, 677 (1992))

EBV (Thorley-Lawson et al., Cell 30, 415 (1982))

HTLV (Robert-Garoff et al., J. Virol. 53, 214 (1985), Matsushita et al., J. Virol. 62, 2107 (1988)).

In addition, the ligands also include monoclonal or polyclonal antibodies or antibody fragments which bind, by their constant domains, to Fc-γ- or [lacuna] receptors of immune cells (Rojanasakul et al., Pharm. Res. 11, 1731 (1994)).

The murine monoclonal antibodies should preferably be employed in humanized form. The humanization is effected in the manner described by Winter et al. (Nature 349, 293 (1991)) and Hoogenbooms et al. (Rev. Tr. Transfus. Hemobiol. 36, 19 (1993)). Antibody fragments are prepared in accordance with the state of the art, for example in the manner described by Winter et al. (Nature 349, 293 (1991), Hoogenboom et al. (Rev. Tr. Transfus. Hemobiol. 36, 19 (1993), Girol (Mol. Immunol. 28, 1379 (1991) and Huston et al. (Int. Rev. Immunol. 10, 195 (1993).

The ligands furthermore include all substances which bind to membrane structures or membrane receptors on the surface of the virus-infected cells. These substances include, for example, growth factors, such as cytokines, EGF, TGF, FGF or PDGF, or their fragments or constituent sequences thereof, which bind to receptors which are expressed by cells of this nature.

Ligands are also included in this regard which bind to cell membrane structures which are selective for particular tissues. These include, for example:

| Membrane structure | Ligands | Tissue cells |
|---|---|---|
| Asialoglycoprotein receptor | Asialoorosomucoid Neoglycoprotein Galactose | Liver cells |
| Transferrin receptor | Transferrin | Liver, other tissue cells |
| Insulin receptor | Insulin | Liver cell, other tissue cells |
| Mannose 6-phosphate receptor | Mannose | Macrophages in spleen, liver, lung and other tissues |
| Fc-γ receptors | Immunoglobulin G | Reticuloendothelial system and other tissues |

These ligands and membrane structures are reviewed in Perales et al., Eur. J. Biochem. 226, 255 (1994).

All substances which bind to cell membrane structures of macrophages and/or lymphocytes are suitable for use as ligands for the prophylaxis of infectious diseases. Ligands of this nature have already been described in section 6.4.

8.5. Choice of the ligands for an active compound for the prophylaxis of infectious pathogens Substances which bind specifically to the surface of macrophages and/or lymphocytes are preferred as ligands for viral and non-viral vectors, for example in colloidal dispersions or in polylysine/ligand complexes. Ligands of this nature have already been described in section 6.4.

These ligands are components of the vectors. However, within the meaning of this invention, ligands can also be admixed with the vectors. For this admixture, use should particularly be made of ligands which are able to activate macrophages and/or lymphocytes. These ligands include, for example:

cytokines, such as IL-1α, IL-1β, IL-2, IL-3, IL-4, IL-5, IL-6, IL-10, IL-12, IFN-γ, GM-CSF or M-CSF
      (Hadden, Int. J. Immunopharm. 16, 703 (1994)) and
   soluble cytokine receptors, such as the IL-4 receptor.

Alternatively or additionally, adjuvants can be mixed in as well. Examples of these adjuvants are:

synthetic adjuvants
      (Reviews in: Parant, nt. J. Immunopharm. 16, 445 (1994) and Cernescu, Int. J. Immunopharm. 16, 369 (1994))
   liposomes
      (Reviews in: Alving, J. Immunol. Methods 140, 1 (1991) and BBA 1113, 307 (1992) and Sato and Sanamoto, Prog. Lipid Res. 31, 345 (1992))

lipopolysaccharides or lipid A
(Review in : Alving, Immunol. 187, 430 (1993))
biodegradable polymers, such as
poly(DL-lactides-Co-glycolides)
(Eldridge et al., Infect. Immun. 59, 2978 (1991))
pseudolatexes
(Coffin and McGiuity, Pharmaceut. Res. 9, 200 (1992))
muramyl dipeptides
(Morim et al., Int. J. Immunopharm. 16, 451 (1994)).

In addition, it is within the meaning of the invention to admix substances with the vectors which make the vectors suitable for being taken up via the mucosal membrane and for, for example, oral immunization.

Substances and formulations of this nature have been reviewed by Walker (Vaccine 12, 387 (1994)).

8.6 Preparation of the active compound against viral infections

The preparation of the novel active compound is described in more detail with the aid of the following examples:

a) Construction of the chimeric promoter HIV-LTR-TAR-CDE-CHR-Inr

Figure 13:
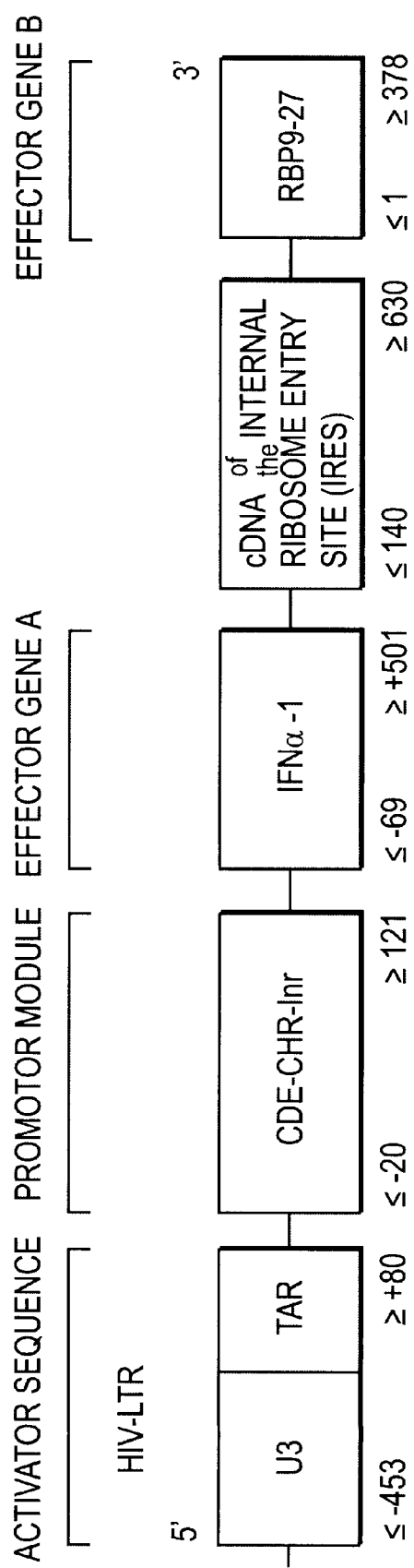

The HIV-LR-TAR promoter (position ≦−453 to ≧+80 (Rosen et al., Cell 41, 813 (1985)) is linked, at its 3' end, to the 5' terminus of the CDE-CHR-Inr module of the human cdc25C gene (position ≦−20 to ≧+121, Lucibello et al., EMBO J., 14, 132 (1995)) (FIG. 13). The linking is effected using enzymes which are known to the skilled person and which are commercially available.

b) Construction of a plasmid which contains the chimeric promoter HIV-LTR-TAR-CDE-CHR-Inr in the central component of the active compound The described chimeric promoter module-transcription unit is linked, at its 3' end, to the 5' terminus of a DNM which contains the complete coding region of interferon α-1 (position ≦−69 to ≧+501, (Streuli et al., Science 209, 1343 (1980)). This DNA also contains the signal sequence which is necessary for secretion. Transcription control units and the DNA for interferon α-1 are cloned into pUC19/19 or Bluescript-derived plasmid vectors which can be used for in-vivo administration either directly or in colloidal dispersion systems. Alternatively, the chimeric genes can be transferred into viral vectors, or other suitable vectors, and injected.

c) Construction of a plasmid which contains two genes for active substances

The HIV-LTR-TAR-CDE-CHR-Inr transcription unit, as described in a), is linked, at its 3' end, to the 5' end of the DNA for interferon a-1 (position ≦−69 to ≧+501; Streuli et al., Science 209, 1343 (1980)). The linking is effected using enzymes which are known to the skilled person and which are commercially available. The 3' end of the DNA for interferon α-1 is now linked to the 5' end of the cDNA of the internal ribosome entry site (position ≦140 to ≧630; Pelletier and Sonenberg, Nature 334, 320 (1988-)), and their 3' end is exclusively linked to the 5' end of the DNA for the Rev-binding protein (RbP9-27) (position ≦1 to ≧378, Reid et al., PNAS USA 86, 840 (1989)) (see FIG. 13). The active compound which has been prepared in this way is then cloned into puc18/19 or into Blue-script-derived plasmid vectors which can be used for in-vivo administration, either directly or in colloidal dispersion systems. Alternatively, the chimeric genes can be transferred into viral vectors, or other suitable vectors, and injected.

9) Preparation of an Active Compound Against leukemias (and lymphomas)

9.1. Choice of the activator sequence for leukemias

A nucleotide sequence (promoter sequence or enhancer sequence) with which transcription factors which are formed or are active in leukemia cells interact is envisaged as the activator sequence (UAS=upstream activator sequence).

However, within the meaning of this invention, the preferred activator sequences include gene-regulatory sequences or elements from genes which encode proteins which are formed, in particular, in leukemia cells.

These activator sequences include, for example, the promoter sequences, which are cited in the following literature references, for genes which encode the following proteins:

c-myc
(Bentley et al., Mol. Cell. Biol. 6, 3481 (1986), Lang et al., Oncogene 6, 2067 (1991), Meulia et al., Mol. Cell. Biol. 12, 4590 (1992), Desjardins, Mol. Cell. Biol. 13, 5710 (1993))

HSP-70
(Taira et al., BBA 1130, 166 (1992))

bcl-1/cyclin D-1
(Herber et al., Oncogene 9, 1295 (1994))

bcl-2
(Young et al., Mol. Cell. Biol. 13, 3686 (1993))

IL-6
(Droogmans et al., DNA-Sequence 3, 115 (1992), Mori et al., Blood 84, 2904 (1994), Liberman et al., Mol. Cell. Biol. 10, 2327 (1990), Ishiki et al., Mol. Cell. Biol. 10, 2757 (1990))

Il-10
(Kim et al., J. Immunol. 148, 3618 (1992), Kube et al., Cytokine 7, 1 (1995), Platzer et al., DNA-Sequence 4, 399 (1994), Kube et al., Cytokine 7, 1 (1995))

NFα, TNFβ
(Sidhu et al., Pharmac. Ther. 57, 79 (1993), Vilcek et al., J. Biol. Chem. 266, 7313 (1991), Tahashiba et al., Gene 131, 307 (1993), Nedwin et al., Nucl. Acids Res. 13, 6361 (1985), Paul et al., J. Virol. 64, 5412 (1990), Shakhov et al., J. Exp. Med. 171, 35 (1990), van der Ake et al., Nucleic Acids Res. 21, 5636 (1993)).

In addition, these activator sequences include binding sequences for proteins which are formed by the following genes:

HOX-11
(Dear et al., PNAS USA 90, 4431 (1990))

BCR-Abl
(Zhu et al., Nucl. Acid Res. 18, 7119 (1990), Shah et al., Mol. Cell. Biol. 11, 1854 (1991))

E2A-PBX-1
(Monica et al., Mol. Cell. Biol. 14, 8304 (1994), Numata et al., Leukemia 7, 1441 (1993), von Dijk et al., PNAS USA 90, 6061 (1993))

PML-RARA
(Promyelocytic leukemia—retinoic acid receptor)
(Potter et al., Leukemia 7, 1302 (1993), Yoshida et al., Genes, Chromosomes Cancer 12, 37 (1995), Brand et al., Nucl. Acids Res. 18, 6799 (1990))

c-myc
c-myc proteins bind to, and activate, multimers of the nucleotide sequence (5'-GGAAGCAGACCACGTGGTCTGCTTCC-3') (SEQ ID NO:10) which is termed an Myc E-box (Blackwood and Eisneman, Science 251, 1211 (1991))

9.2. Choice of the active substance for leukemias

Within the meaning of the invention, an active substance is to be understood as being a DNA sequence whose expressed protein inhibits the proliferation of cells, in particular also of leukemia cells. These cell cycle inhibitors include, for example, the DNA sequences for inhibitory cytostatic and cytotoxic proteins and enzymes, as have already been described in section 6.2. e-g).

In addition, a cell cycle inhibitor is to be understood as being a DNA sequence which expresses a protein which, directly or indirectly, exhibits a cytostatic or cytotoxic effect on leukemias. Proteins of this nature include, for example:

IL-1α
(Fenton, Int. J. Immunopharm. 14, 401 (1992), Furntani et al., Nucl. Acids Res. 14, 3167 (1986), Lafage et al., Blood 73, 104 (1989), March et al., Nature 315, 641 (1985))

IL-1β
(Bensi et al., Gene 52, 95 (1987), Auron et al., PNAS 81, 7907 (1984), Clark et al., Nucl. Acids Res. 14, 7897 (1986))

IL-2
(Fletscher et al., Lymphok. Res. 6, 45 (1987), Matsui et al., Lymphokines 12, 1 (1985), Tanaguchi et al., Nature 302, 305 (1983))

IL-4
(Lee et al., PNAS 83, 2061 (1986): Paul, Blood 77, 1859 (1991), Yokota et al., PNAS USA 83, 5894 (1986), von Leuven et al., Blood 73, 1142 (1989), Arai et al., J. Immunol. 142, 274 (1989))

IL-10
(Vieira et al., PNAS USA 88, 1172 (1991), Moore et al., Science 248, 1230 (1990), Kim et al., J. Immunol. 148, 3618 (1992))

IL-12
(Gubler et al., PNAS USA 88, 4143 (1991), Wolf et al., J. Immunol. 146, 3074 (1991), Kobayashi et al., J. Exp. Med. 170, 827 (1989), Gately et al., J. Immunol. 147, 874 (1991;, Schoenhaut et al., J. Immunol. 148, 3433 (1992), interferons, such as
IFNα (Henco et al., J. Mol. Biol. 185, 227 (1985), Pestka et al., Annu. Rev. Biochem. 56, 727 (1987), Weissmann et al., Phil. Trans. R. Soc. Lond. B299, 7 (1982), Goeddel et al., Nature 290, 20 (1981))
IFNβ (Sen et al., J. Biol. Chem. 267, 5017 (1992), Mark et al. EP 192.811, EP 234.599, US 4588.585
IFN-γ (Gray et al., Nature 295, 503 (1982), Yip et al., PNAS USA 79, leukemia inhibitory factor (LIF)
(Metcalf, Int. J. Cell Clon. 9, 85 (1991), Sutherland et al., Leuk. 3, 9 (1989), Gough et al., PNAS USA 85, 2623 (1988), Gough et al., Ciba Found. Symp. 167, 24 (1992), Stahl et al., J. Biol. Chem. 265, 8833 (1990), Rathjan et al., Cell 62, 1105 (1990))

TNF
(Porter TiBTech 9, 158 (1991); Sidhu et al., Pharmac. Ther. 57, 79 (1993)) in particular
TNFα (Beutler et al., Nature 320, 584 (1986), Kriegler et al., Cell 53, 45 (1988))
TNFβ (Gray et al., Nature 312, 721 (1984), Li et al., J. Immmunol. 138, 4496 (1987), Aggarwal et al., J. Biol. Chem. 260, 2334 (1985))

TGFβ
(Kehrl et al., J. Immunol. 137, 3855 (1986), J. Exp. Med. 163, 1037 (1986), Ten Dikje et al., PNAS USA 85, 4715 (1988), Derynck et al., EMBO J. 7, 3737 (1988), Massague, Ann. Rev. Cell Biol. 6, 597 (1990), Kondiah et al., J. Biol. Chem. 265, 1089 (1990), Garnier et al., J. Mol. Biol. 120, 97 (1978))

oncostatin M
(Brown et al., J. Immunol. 147, 2175 (1991); Grove et al., J. Biol. Chem. 266, 18194 (1991), Hamilton et al., Biochem. Biophys. Res. Commun. 180, 652 (1991), Malik et al., Mol. Cell. Biol. 9, 2847 (1989), Kallstad et al., J. Biol. Chem. 266, 8940 (1991)

However, within the meaning of the invention, DNA sequences of fusion proteins formed between the listed cytokines and growth factors, or the extra-cellular moiety of the receptors, on the one hand, and the Fc moiety of human immunoglobulin, on the other hand, can also be used as active substance. DNA sequences of this nature, and their preparation, have been described in EP 0464 633 A1.

The choice of the cell cycle inhibitor depends on the type of leukemia.

Thus, IL-4 and IL-6 have a particularly strong antiproliferative effect in B-CLL (von Kooten et al., Leuk. Lymph. 12, 27 (1993)).

TGFβ preferentially inhibits lymphocyte proliferation (Kehrl et al., J. Immunol. 143, 1868 (1989)).

TNF, in particular TNF , inhibits myeloid leukemia cells (Porter, FEMS Microbial. Immunol. 64, 193 (1990) and lymphoma cells (Sidhu et al., Pharm. Therp. 57, 79 (1993)).

IFN-γ inhibits myeloma cells (Portier et al., Blood 81, 3076 (1993)).

IFNα inhibits hair cell leukemia (Gutterman, PNAS USA 91, 1198 (1994)), and also non-Hodgkin lymphomas (Solal-Celigny et al., New Engl. J. Med. 329, 1608 (1993), CLL, T-CLL, CML and ALL (Gutterman, PNAS USA 91, 1198 (1994), Dorr, Drugs 45, 177 (1993)).

LIF inhibits the proliferation of CML cells (Metcalf, Int. J. Cell. Clon. 9, 95 (1991)).

IL-10 induces apoptosis in B-CLL cells (Fluchinger et al., J. Exp. Ned. 179, 91 (1994)).

On the other hand, IL-1, IL-2, IL-4, IL-12 or interferons, in particular, can, by activating immune cells which are adjacent to the transduced leukemia cells, trigger an inflammatory reaction (Fenton et al., Int. J. Immunopharm. 14, 401 (1992), Janssen et al., Cancer Immunol. Immunother. 39, 207 (1994), Kirchner, DMW 111, 64 (1986), Paul, Blood 77, 1859 (1991), Gateley et al., Cancer Invest. 11, 500 (1993)) which destroys the leukemia cells.

However, a prerequisite for using the DNA sequence of one of the listed cytokines as a cell cycle inhibitor in the active compound is that it has been checked, before the active compound is administered, that the cell cycle inhibitor which has been selected is not a growth factor for the leukemia cells of the particular patient concerned.

9.3. Combination of identical or different active substances for leukemias

The invention furthermore relates to an active compound in which a combination of the DNA sequences of two identical cell cycle inhibitors (A,A) or two different cell cycle inhibitors (A,B) is present. The cDNA of an internal ribosome entry site (IRES) is preferably intercalated, as a regulatory element, for expressing the two DNA sequences.

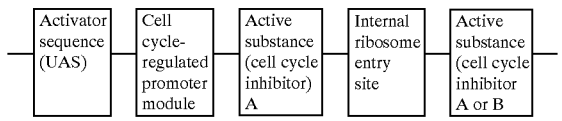

IRESs of this nature have been described, for example, by Montford and Smith (TIB 11, 179, (1995), Kaufman et al., Nucl. Acids Res. 19, 4485 (1991), Morgan et al., Nucl. Acids Res. 20, 1293 (1992), Dirks et al., Gene 128, 247 (1993), Pelletier and Sonenberg, Nature 334, 320 (1988) and Sugitomo et al., BioTechn. 12, 694 (1994).

Thus, the cDNA of the IRES sequence of poliovirus (position $\leq 140$ to $\geq 630$ of the 5' UTR) can be used to link the DNA of cell cycle inhibitor A (at the 3' end) and the DNA of cell cycle inhibitor B (at the 5' terminus).

Depending on the combination, an active compound of this nature exhibits either an additive (A+A, A+b1) or synergistic effect within the meaning of the invention.

9.4. Choice of the ligand for leukemias

Substances which bind to the surface of leukemia cells are preferred as ligands for viral vectors or non-viral vectors, for example in polylysine/ligand conjugates. These substances include antibodies or antibody fragments which are directed against membrane structures of leukemia cells. A large number of such monoclonal antibodies have already been described for diagnostic and therapeutic methods (reviews in Kristensen, Danish Medical Bulletin 41, 52 (1994), Schranz, Therapia Hungarica 38, 3 (1990), Drexler et al., Leuk. Res. 10, 279 (1986), Naeim, Dis. Markers 7, 1 (1989), Stickney et al., Current Op. Oncol. 4, 847 (1992), Drexler et al., Blut 57, 327 (1988) and Freedman et al., Cancer Invest. 9, 69 (1991)). Depending on the type of leukemia, the following monoclonal antibodies, or their antigen-binding antibody fragments, are, for example, suitable for use as ligands:

| Cells | Membrane antigen | Monoclonal antibodies described by |
|---|---|---|
| AML | CD13 | Kaneko et al., Leuk. Lymph. 14, 219 (1994) |
| | | Muroi et al., Blood 79, 713 (1992) |
| | CD14 | Ball, Bone Marrow Transplant. 3, 387 (1988) |
| | CD15 | Guyotat et al., Bone Marrow Transplant. 6, 385 (1990) |
| | | Campos et al., Eur. J. Cancer 28, 37 (1992) |
| | CD33 | Jurcic et al., Leukemia 9, 244 (1995), Caron et al., Cancer 73, 1049 (1994) |
| | CAMAL | Shellard et al., Exp. Hematol. 19, 136 (1991) |
| | sialosyl-Le | Muroi et al., Blood 79, 713 (1992) |
| B-CLL | CD5 | Kaminski et al., Cancer Treat. Res. 38, 253 (1988) |
| | | Tassone et al. Immunology Lett. 39, 137 (1994) |
| | CD1c | Orazi et al., Eur. J. Haematol. 47, |
| | CD23 | 28 (1991) |
| | Idiotypes and isotypes of the membrane immunoglobulins | Schroeder et al., Immunol. Today 15, 289 (1994) |
| T-CLL | CD33 M38 | Imai et al., J. Immunol. 151, 6470 (1993) |
| | IL-2 receptors | Waldmann et al., Blood 82, 1701 (1993) |

-continued

| Cells | Membrane antigen | Monoclonal antibodies described by |
|---|---|---|
| | T cell receptors | |
| ALL | CALLA | Morishima et al., Bone Marrow Transplant. 11, 255 (1993) |
| | | Anderson et al., Blood 80, 84 (1993) |
| | CD19 non-Hodgkin lymphoma | Okazaki et al., Blood 81, 84 (1993) |

The murine monoclonal antibodies should preferably be employed in humanized form. The humaization is effected in the manner described by Winter et al., (Nature 349, 293 (1991)) and Hoogenboom et al., (Rev. Tr. Transfus. Hemobiol. 36, 19 (1993)). Antibody fragments are prepared in accordance with the state of the art, for example in the manner described by winter et al., Nature 349, 293 (1991), Hoogenboom et al., Rev. Tr. Transfus. Hemobiol. 36, 19 (1993), Girol. Mol. Immunol. 28, 1379 (1991) or Huston et al., Int. Rev. Immunol. 10, 195 (1993).

In addition, the ligands include all active compounds which bind to membrane structures or membrane receptors of leukemia cells. These include, for example, growth factors, or their fragments or constituent sequences thereof, which bind to receptors which are expressed by leukemia cells.

Growth factors of this nature have already been described (reviews in Cross et al., Cell 64, 271 (1991), Aulitzky et al., Drugs 48, 667 (1994), Moore, Clin. Cancer Res. 1, 3 (1995) and Van Kooten et al., Leuk. Lymph. 12, 27 (1993)). For example, they include:

IFNα in non-Hodgkin lymphomas (Hiddemann et al., Blood Rev. 8, 225 (1994))

IL-2, particularly in T cell leukemias (Waldmann, J. Nat. Cancer Inst. 81, 914 (1989), Kreitman et al., Int. J. Immunopharm. 14, 465 (1992)

FGF in T cell leukemias, monocytic leukemias, myeloid leukemias, erythroid leukemias and megacaryoblastic leukemias (Armstrong et al., Cancer Res. 52, 2004 (1992)

TGFβ in leukemias (Keller et al., J. Cell Biochem. 39, 79 (1989))

Retinoids, e.g. retinoic acid in acute promyelocytic leukemia (Cornic et al., Anticancer Res. 14, 2339 (1994)).

9.5. Preparation of the active compound for leukemias

Figure 14:
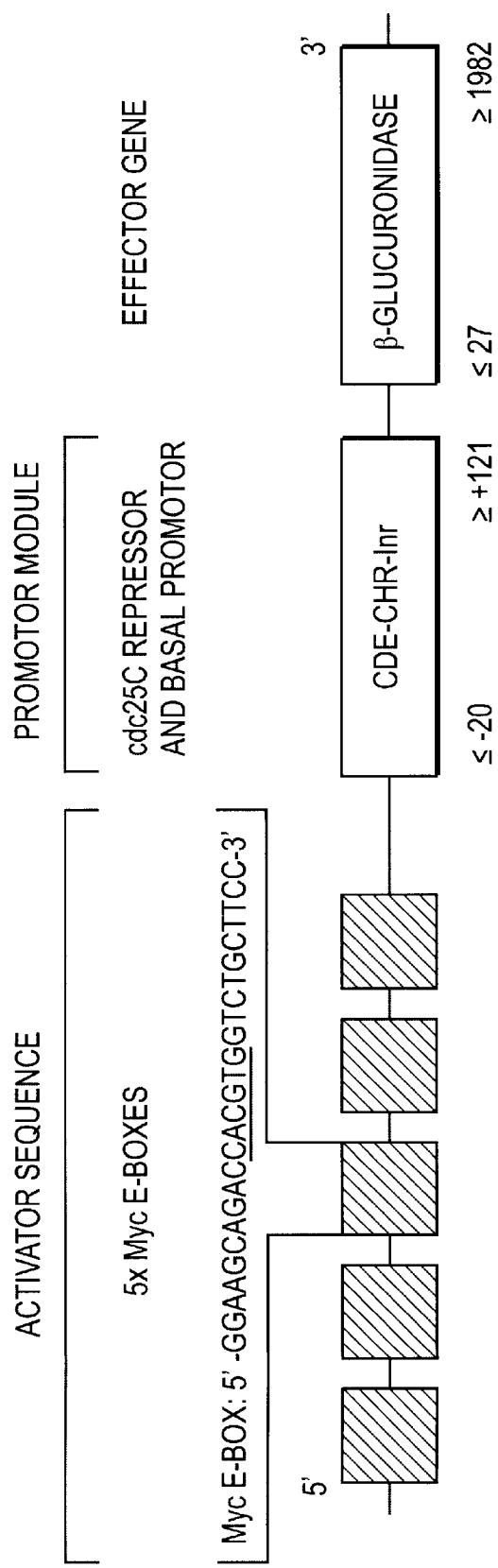

The preparation of the active compound is clarified using the following examples:

a) Construction of chimeric promoter mycE box-CDE-CHR-Inr 5 copies of the human mycE box (nucleotide sequence 5'-GGAAGCAGACCACGTGGTCTGCTTCC-3 (SEQ ID NO:10); Blackwood and Eisenman, Science 251, 1211 (1991)) are linked to each other in the 5'-3' orientation and connected, at their 3' end, to the 5' terminus of the CDE-CHR lnr module of the human cdc25 gene (position −20 to $>\_+121$ of that of Lucibello et al., EMBO J. 14, 132 (1995)) (see FIG. 14).

The linkings are effected using enzymes which are known to the skilled person and are commercially available. The myc E box-promoter module-transcription unit which has been prepared in this way is linked, at its 3' end, to the 5' terminus of a DNA which contains the complete coding region of human β-glucuronidase (DNA position $\leq 27$ to $\geq 1982$, of that of Oshima et al., PNAS USA 84, 684 (1987)) (see FIG. 14).

This DNA also contains the signal sequence (22N terminal amino acid) which is necessary for secretion. In order to facilitate secretion from the cell, this signal sequence should preferably be replaced with the immunoglobulin signal sequence (position ≦63 to ≧107; Riechmann et al., Nature 332, 323 (1988), see FIG. 15). Transcription control units and the DNA for human β-glucuronidase are cloned into pUC18/19 or bluescript-derived plasmid vectors which can be used, either directly or in colloidal dispersion systems, for in-vivo administration. Alternatively, the chimeric genes can be transferred into viral vectors, or other suitable vectors, and injected.

10) Activity of the Active Compound

Following local (e.g. intissues, body cavities, gastrointestinal tract, tissue interstices, articular spaces or cytokines) or systemic, preferably intravenous or intraarterial, administration, an active compound according to the present invention makes it possible to achieve an effect, mainly if not exclusively, on the target cells since the combination of tissue-specific activator sequence and cell cycle-regulated promoter module ensures that the active substance is expressed largely or exclusively in dividing target cells.

Long-term relief of hematopoietic cytopenias and significant alleviation of allergies and autoimmune diseases can thereby be achieved. In the case of chronic joint inflammations, intraarticular injection of the active compound brings about inhibition of synovial cell proliferation. The active compound can achieve a therapy in the case of chronic viral infections. In addition, the active compound offers an effective and safe option for vaccinating against infectious pathogens. In the case of leukemias, there is the prospect of a therapeutic effect.

Since the active compound promises a high degree of safety, both on the basis of its cell specificity and its cell cycle specificity, it can also be employed for prophylaxis or therapy in high doses and, if necessary, repeatedly at intervals of days, weeks or months.

Legends to FIGS. 1–15:

FIG. 1:

Nucleotide sequence of the cdc25C promoter region (SEQ ID NO:1) with the protein-binding sites which have been found in vivo (genomic DNS footprinting;. (filled circles): complete constitutive protection; o (open circles): partial consititutive protection; *(asterisks): cell cycle-regulated, G1-specific protection). CBS: constitutive binding site; CDE: cell cycle-dependent element. Regions with a grey underlay indicate the $Y_c$ boxes (NF-Y binding sites). Start sites are marked by filled squares.

FIG. 2:

Depression of the cdc25C promoter specifically in $G_0$ by mutation of the cdc.

FIG. 3:

Diagramatic representation of the regulation of the cdc25C enhancer by the CDE.

FIG. 4:

$G_0/G_1$—specific repression of the SV40 enhancer by the CDE.

FIG. 5:

Homologies in the CDF-CHR region and the 5' Yc boxes in the cdc25C (SEQ ID NOS:2 and 3), cyclin A (SEQ ID NOS:6 and 7) and cdc2 (SEQ ID NOS:4 and 5) promoters.

FIG. 6:

Chimeric promoters for expressing thrombopoietin. Position indications relate to the following literature:

| | |
|---|---|
| SCF receptor promoter: | Yamamoto et al., Jpn. J. Cancer Res. 84, 1136 (1993) |
| IL-1 receptor promoter: | Ye et al., PNAS USA 90, 2295 (1993) |
| IL-3 receptor (α)-promoter: | Miyajima et al., Blood 85, 1246 (1995) |
| GM-CSF receptor (α)-promoter: | Nakagawa et al., J. Biol. Chem. 269, 10905 (1994) |
| β-chain (IL-3 receptor/GM-CSF): | Gorman et al., J. Biol. Chem. 267, 15842 (1992) |
| CDE-CR-Inr: | Lucibello et al., EMBO J. 14, 132 (1995) |
| IL-3: | Yang et al., Cell 47, 3 (1986) |
| internal ribosome entry site: | Pelletier and Sonenberg, Nature 334, 320 (1988) |
| thrombopoietin: | de Sauvage et al., Nature 369, 533 (1994) |

FIG. 7:

Chimeric promoters for the prophylaxis or therapy of autoimmune diseases and/or allergies. Position indications relate to the following literature:

| | |
|---|---|
| IL-2 promoter: | Williams et al., J. Immunol. 141, 662 (1988) |
| IL-1 receptor promoter: | Ye et al., PNAS USA 90, 2295 (1993) |
| CDE-CHR-Inr: | Lucibello et al., EMBO J. 14, 132 (1995) |
| IL-10: | Moore et al., Science 248 1230 (1990) |
| internal ribosome entry site: | Pelletier and Sonenberg, Nature 334, 320 (1988) |
| β-Glucoronidase: | Oshima et al., PNAS USA 84, 685 (1985) |
| immunoglobulin signal sequence: | Riechmann et al., Nature 332, 323 (1988) |

FIG. 8:

Diagrammatic representation of the exonuclease III truncations of the 5'-flanking TIMP-3 gene region. In order to facilitate sequencing, approximately 1600 bp of the 5'-flanking TIMP-3 gene region were truncated from the 5' end by being treated with exonuclease III and cloned into the Bluescript SK(−) vector. The names of the plasmids designate their 5' truncation (e.g. Δ−1300 contains 1300 bp 5' of the transcription start site). The transcription start site is marked by +1.

FIG. 9:

Nucleotide sequence of 500 bp of the human TIMP-3 promoter and 101 bp of the 5'-untranslated region (SEQ ID NO:8). GC boxes (Sp1 binding sites), two half sides of a possible NF1 binding site and an element resembling the C/EBP binding site are labelled. The transcription start site is marked by an arrow.

FIG. 10:

Induction kinetics of the Δ−1010-TIMP-3 promoter-luciferase construct following stimulation of resting NIH3T3 cells with 20% FCS.

Graphic representation. Following the DEAE transfection of 7 μg of plasmid DNA, the NIH3T3$^{RT}$ cells were incubated in serum-free medium for 40 h and stimulated with 20% FCS; expression of the luciferase reporter gone was then determined at the given times.

Figure 11A:
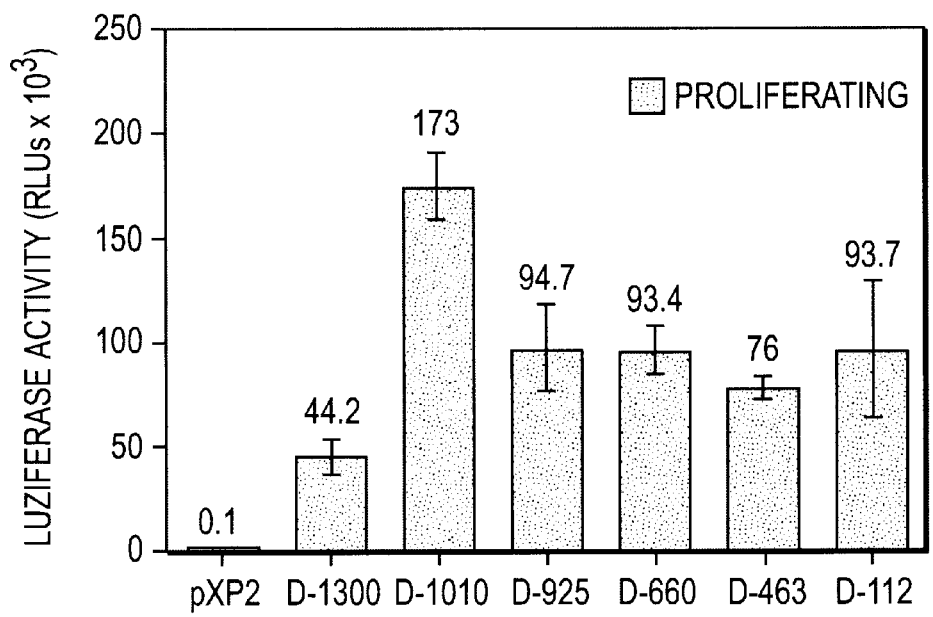
Figure 11B:
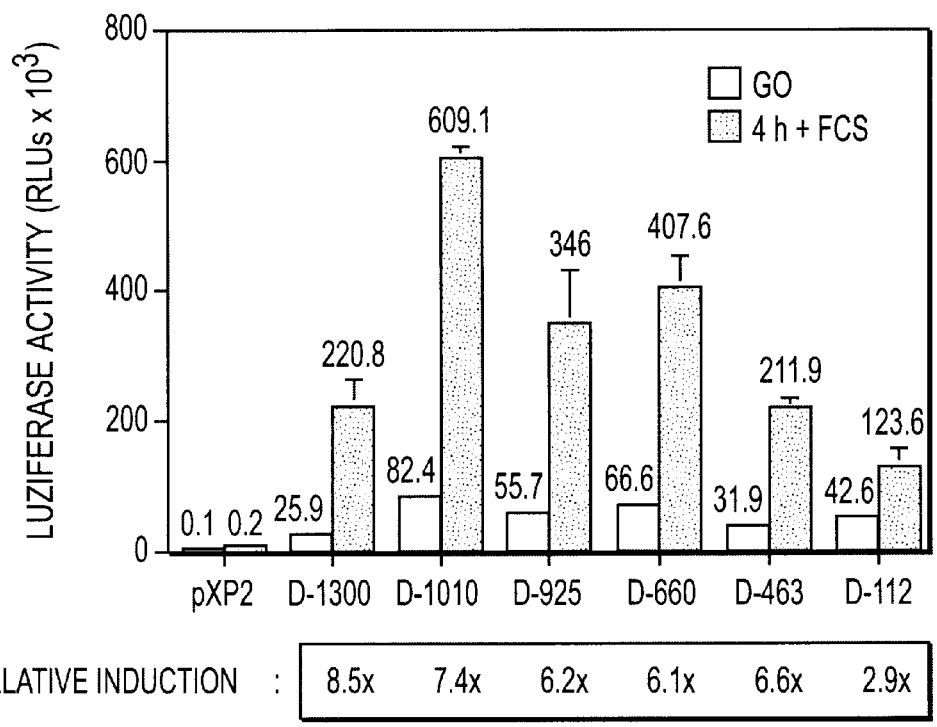
Figure 12:
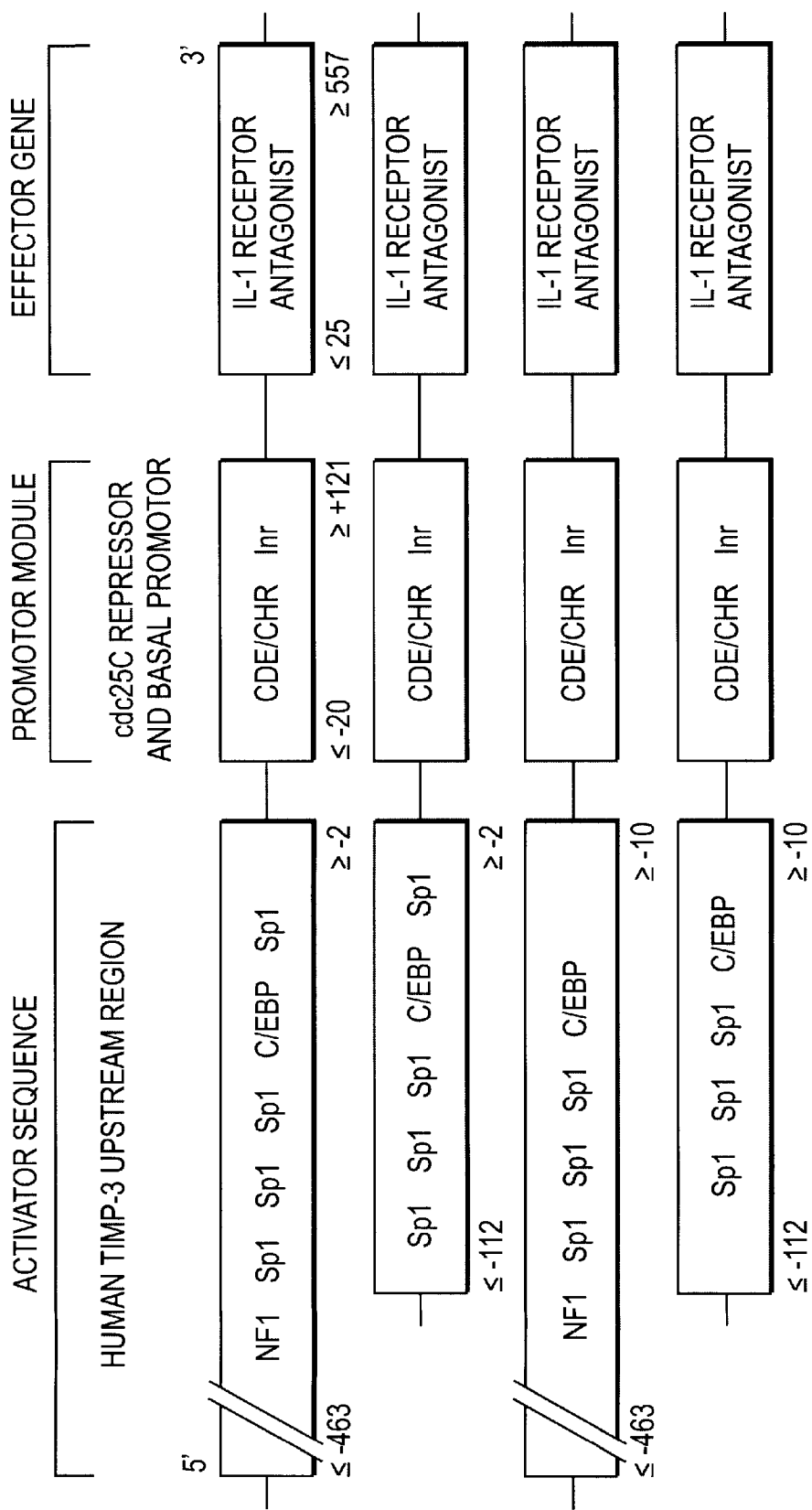

FIGS. 11a and 11b:

Transient expression analysis of 5'-truncated TIMP-3 promoter-luciferase constructs in normally growing, resting and serum-stimulated NIH3T3$^{RT}$ cells.

The plasmids were named in accordance with their truncations (see FIG. 8)

(a) Analysis in normally growing NIH3T3 cells (b) Analysis of the same constructs as in (a) in resting NIH3T3 cells as compared with NIH3T3 cells which were stimulated with 20% FCS for 4 h.

As described in Tab. 1, the experiments in (a) and (b) were carried out three times using plasmid DNAs which were prepared independently of each other. Standard deviations are depicted as thick lines. Absence of the thick lines indicates a standard deviation which is very low and can no longer be depicted in the graph.

FIG. 12:

Chimeric constructs consisting of different moieties of the human TIMP-3 promoter, the 3'-fused promoter module containing the CDE and CHR repressor elements and a DNA for the IL-1 receptor antagonist (complete coding region) as effector. Position indications refer to the main start site of the TIMP-3 gene, to the system for cdc25C which was used by Lucibello et al. (EMBO J. 15, 132 (1995)) and to positions in the IL-1 receptor antagonist DNA (Eisenberg et al., Nature 343, 341 (1990)).

FIG. 13:

Chimeric promoters for the therapy of HIV infection The position indications relate to the following literature:

| | |
|---|---|
| HIV-LTR | (Rosen et al., Cell 41, 813 (1985)) |
| CDE-CHR-Inr | (Lucibello et al., EMBO J. 14, 132 (1995)) |
| IFN α | (Streuli et al., Science 209, 1343 (1980)) |
| IRES | (Pelletier and Sonenberg, Nature 334, 320 (1988)) |
| RBP9-27 | (Reid, PNAS USA 86, 840 (1989)) |

FIG. 14:

Chimeric constructs consisting of 5 mycE boxes (Blackwood and Eisenman, Science 251, 1211 (1991)), the 3'-fused cdc25C basal promoter containing the CDE and CHR repressor elements and a DNA for β-glucuronidase (complete coding region) as effector.

Position indications refer to the system for cdc25C used by Lucibello et al., (1995) or to positions in the β-glucuronidase DNA (Oshima et al., 1987).

FIG. 15:

Position indications for the immunoglobulin (HuVHCAMP) signal sequence (MGWSCIILFLVATAT) (SEQ ID NO:11) refer to Riechmann et al., Nature 332, 323 (1988)

B) Alternative: Incorporation of the Ig signal peptide for improving the extracellular secretion of the β-glucuronidase.

TABLE 1

Role of CDE and CHR in the cell cycle-regulated transcription of cdc25C, cyclin A and cdc2

| Tab. 1 | $G_0$ | Growing | Factor |
|---|---|---|---|
| wt | | | |
| cdc25C | 0.8 | 13.1 | 17.5 |
| cyclin A | 0.7 | 27.1 | 41.7 |
| cdc2 | 1.0 | 41.2 | 41.2 |
| mCDE(−13) | | | |
| cdc25C | 7.6 | 11.6 | 1.5 |
| cyclin A | 13.4 | 23.9 | 1.8 |
| cdc2 | 11.3 | 33.9 | 3.0 |
| mCHR(−6/−3) | | | |
| cdc25C | 14.4 | 21.0 | 1.5 |
| cyclin A | 15.5 | 28.3 | 1.8 |
| cdc2 | 18.6 | 38.6 | 2.1 |

Result of transient transfections in HIH3T3 cell are depicted as RLUs/1000. mCDE: mutated CDE (Pos. -13: G→T); mCHR: mutated CHR (Pos. -6 to -3).

Tab 2: Expression of different promoter-luciferase constructs in normally proliferating (A) and serum-stimulating (B) NIH3T3 cells. Following DEAE transfection of 7 μg of plasmid DNA, the NIH3T3 cells were incubated in serum-containing (A) or serum-free (B) medium for 40 h and stimulated (B) with 20% FCS for 4 h and the expression of the luciferase reporter gene was then determined.

TABLE 2

| A. Expression in proliferating cells ($RLU \times 10^3$) | |
|---|---|
| TIMP-3 Δ-1010 | 189.5 ± 6.4 |
| pRSV-LTR | 308.1 ± 23.4 |
| p5 × TRE | 59.1 ± 2.2 |
| Cyclin D1 Δ-973 | 27.8 ± 3.5 |
| pXP2 | 0.2 |
| B. Relative induction by 20% FCS in FCB-stimulated cells as compared with G0 cells (Factor) | |
| TIMP-3 Δ-1010 | 8.4 ± 0.4 |
| p5 × TRE | 2.4 ± 0.2 |
| Cyclin D1 Δ-973 | 3.5 ± 0.3 |
| pT81 | 1.0 ± 0.2 |
| pXP2 | 1.2 |

What is claimed is:

1. An active compound comprising a DNA construct which is composed of an activator sequence, a cell cycle-regulated promoter module and a DNA sequence encoding an active substance, wherein said promoter module comprises a cell cycle dependent element, a cell cycle homology region, and an initiation site.

2. The active compound as claimed in claim 1, in which the promoter module comprises the CDE-CHR-Inr elements and contains positions $\leq-20$ to $\geq+30$ of the cdc25C promoter region, thereby comprising the nucleotide sequence of SEQ ID NO: 12, where CDE constitutes the cell cycle-dependent element comprising the nucleotide sequence TGGCGG, CHR constitutes the cell cycle gene homology region comprising the nucleotide sequence GTTTGAA and Inr constitutes the initiation site at position +1.

3. The active compound as claimed in claim 1, containing an activator sequence (promoter sequence or enhancer sequence) which is regulated by transcription factors which are formed to a particularly great degree in cells of the hematopoietic system, in synovial cells, in virus-infected cells, in parasites, in macrophages, in lymphocytes or in leukemia cells.

4. The active compound as claimed in claim 3, containing the CMV promoter sequence, the CMV enhancer sequence or the SV40 promoter sequence.

5. The active compound as claimed in claim 3, in which the activator sequence constitutes the promoter sequence of a gene for a cytokine, or of the receptor for a cytokine, which is activated in immature cells of the hematopoietic system.

6. The active compound as claimed in claim 5, containing the promoter sequence for stem cell factor interleukin (IL)-1α, IL-1β, IL-3, IL-6, LIF or granulocyte macrophage colony stimulating factor, or the respective promoter sequence of the receptors for stem cell factor, IL-1 or IL-3, IL-6, LIF or GM-CSF, or the promoter sequence for interferon regulatory factor 1 (IRF-1).

7. The active compound as claimed in claim 3, in which the activator sequence constitutes the promoter sequence of a gene for a protein which is formed to an increased extent in macrophages or lymphocytes when macrophages or lymphocytes are activated.

8. The active compound as claimed in claim 7, containing the promoter sequence for interleukin (IL)-1α or IL-1β, IL-1 receptor, IL-2, IL-2 receptor, inferon γ, IL-3, IL-3 receptor, IL-4, IL-4 receptor, IL-5, IL-6, interferon regulatory factor 1, IFN-γ responsive promoter, IL-7, IL-8, IL-9, IL-10, IL-11, IL-12, IL-13, granulocyte macrophage colony stimulating factor (GM-CSF), GM-CSF receptor, granulocyte colony stimulating factor (G-CSF), macrophage colony stimulating factor receptor, macrophage scavenger type I or type II receptor or leukemia-inhibiting factor (LIF), LFA-1, MAC-1 or p150.95.

9. The active compound as claimed in claim 1, containing the promoter sequence for interleukin (IL)-1α or IL-1β, IL-1 receptor, IL-2, IL-2 receptor, inferon γ, IL-3, IL-3 receptor, IL-4, IL-4 receptor, IL-5, IL-6, interferon regulatory factor 1, IFN-γ responsive promoter, IL-7, IL-8, IL-9, IL-10, IL-11, IL-12, IL-13, granulocyte macrophage colony stimulating factor (GM-CSF), M-CSF receptor, macrophage scavenger type I or type II receptor, GM-CSF receptor, granulocyte colony stimulating factor (G-CSF) or leukemia-inhibiting factor (LIF), LFA –1, MAC-1 or p150.95.

10. The active compound as claimed in claim 5, wherein the DNA sequence for the active substance encodes erythropoietin, G-CSF, GM-CSF, IL-3, LIF, IL-11 and/or thrombopoietin.

11. The active compound as claimed in claim 1, which contains the DNA sequences of several identical or different active substances, with two DNA sequences being connected to each other through a DNA sequence for the internal ribosome entry site.

12. A vector comprising the active compound as claimed in claim 1.

13. The vector as claimed in claim 12, wherein the vector is a virus.

14. The vector as claimed in claim 13, wherein the virus is a retrovirus, adenovirus, adeno-associated virus, herpes simplex virus or vaccinia virus.

15. A plasmid comprising the active compound as claimed in claim 1.

16. A colloidal dispersion system comprising the active compound as claimed in claim 1.

17. The colloidal dispersion system as claimed in claim 16, wherein the colloidal dispersion system is liposomes.

18. The colloidal dispersion system as claimed in claim 16, wherein the colloidal dispersion system is polylysine ligands.

19. The active compound as claimed in claim 1, further comprising a ligand which binds to membrane structures of hematopoietic cells, to activated lymphocytes, to activated macrophages, to activated synovial cells, to virus-infected cells or to leukemia cells.

20. The active compound as claimed in claim 19, wherein the membrane structures are receptors for cytokines, growth factors, interferons or chemokines.

21. The active compound as claimed in claim 19, wherein said ligand binds to activated synovial cells, activated lymphocytes, activated macrophages or hematopoietic cells by binding to vimentin, fibronectin, IL-1 receptor, IL-2 receptor, TNFα receptor, IL-4 receptor, IL-10 receptor, IGF receptor, TGFβ receptor or mannose 6-phosphate receptor.

22. The vector as claimed in claim 12, wherein the vector is mixed with a cytokine, a cytokine receptor or an adjuvant, or with substances which facilitate uptake and immunization by way of the mucous membrane.

23. The vector as claimed in claim 22, wherein

IL-1α, IL-1β, IL-2, IL-3, IL-4, IL-5, IL-6, IL-10, IL-12, IFNγ, M-CSF, GM-CSF and/or IL-4 receptor, or liposomes, biodegradable polymers, muramyl dipeptides, lipopolysaccharides, lipid A, or $Al(OH)_3$ or $Ca(OH)_3$ are admixed.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 375 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "cdc25c promoter"

(xi) SEQUENCE DESCRIPTION: SEQ ID NO:1:

```
TTCGTGGGGC TGAGGGAACG AGGAAAACAG AAAGGGTGTG GAGATTGGTG AGAGGGAGAG    60

CCAATGATGC GCCAGGCTCC CCGTGAGGCG GAGCTTACCC CGCAGCCTGC CTAACGCTGG   120

TGGGCCAAAC ACTATCCTGC TCTGGCTATG GGCGGGGCA AGTCTTACCA TTTCCAGAGC    180

AAGCACACGC CCCCAGGTGA TCTGCGAGCC AACGATAGG CCATGAGGCC CTGGGCGCGC    240

GCGCGGAGAT TGGCTGACGC AGCTTAGAGG CGAGCGGGA TAGGTTACTG GGCTGGCGGA    300

AGGTTTGAAT GGTCAACGCC TGCGGCTGTT GATATTCTTG CTCAGAGGCC GTAACTTTGG   360

CCTTCTGCTC AGGGA                                                   375
```

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
GCGCGCGGAG ATTGGCTGAC G                                             21
```

(2) INFORMATION FOR SEQ ID NO:3:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

```
GGCGAGCGGG GATAGGT                                                  17
```

(2) INFORMATION FOR SEQ ID NO:4:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

```
CTGGGCTCTG ATTGGCTGCT T                                             21
```

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CGGGCTACCC GATTGGT                                                   17

(2) INFORMATION FOR SEQ ID NO:6:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

CTGTCGCCTT GAATGACGTC A                                              21

(2) INFORMATION FOR SEQ ID NO:7:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

CGAGCGCTTT CATTGGT                                                   17

(2) INFORMATION FOR SEQ ID NO:8:

(i) SEQUENCE CHARACTERISTICS:
(A) LENGTH: 600 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "TIMP-3 Promoter"

(xi) SEQUENCE DESCRIPTION: SEQ ID NO:8:

ATGGCTTCCC ATATCCCAGA GAGTAAGAAC CAGAGAGAGA GAGAGAAAGA GAGAGAGTTT      60

GGGTCTTTCT CCTCTGTGCC TGCTCTCTCC AGAGAAACTG GAGGGGTAGC AGTTAGCATT     120

CCCCCGCTGG TTCCACCAAG CACAGTCAAG GTCTCTAGGA CATGGCCACC CCTCACCTGT     180

GGAAGCGGTC CTGCTGGGGT GGGTGGGTGT TAGTTGGTTC TGGTTTGGGT CAGAGACACC     240

CAGTGGCCCA GGTGGGCGTG GGGCCAGGGC GCAGACGAGA AGGGGCACGA GGGCTCCGCT     300

CCGAGGACCC AGCGGCAAGC ACCGGTCCCG GGCGCGCCCC AGCCCACCCA CTCGCGTGCC     360

CACGGCGGCA TTATTCCCTA TAAGGATCTG AACGATCCGG GGGCGGCCCC GCCCCGTTAC     420

CCCTTGCCCC CGGCCCCGCC CCCTTTTTGG AGGGCCGATG AGGTAATGCG GCTCTGCCAT     480

TGGTCTGAGG GGGCGGGCCC CAACAGCCCG AGGCGGGGTC CCCGGGGGCC CAGCGCTATA     540

TCACTCGGCC GCCCAGGCAG CGGGGCAGAG CGGGCAGCAG GCAGGCGGCG GGCGCTCAGA     600

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "transcription start site"

(xi) SEQUENCE DESCRIPTION: SEQ ID NO:9:

GGGCGGGCCC AACAGCCCG                                                    19

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGAAGCAGAC CACGTGGTCT GCTTCC                                            26

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Met Gly Trp Ser Cys Ile Ile Leu Phe Leu Val Ala Thr Ala Thr
1               5                   10                  15

(2) INFORMATION FOR SEQ ID NO:12:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGCTGGCGGA AGGTTTGAAT GGTCAACGCC TGCGGCTGTT GATATTCTTG                  50

(2) INFORMATION FOR SEQ ID NO:13:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Promoter"

(xi) SEQUENCE DESCRIPTION: SEQ ID NO:13:

ATGGCTTCCC ATATCCCAGA GAGTAAGAAC CAGAGAGAGA GAGAGAAAGA GAGAGAGTTT       60

GGGTCTTTCT CCTCTGTGCC TGCTCTCTCC AGAGAAACTG GAGGGGTAGC AGTTAGCATT       120

CCCCCGCTGG TTCCACCAAG CACAGTCAAG GTCTCTAGGA CATGGCCACC CCTCACCTGT       180

-continued

```
GGAAGCGGTC CTGCTGGGGT GGGTGGGTGT TAGTTGGTTC TGGTTTGGGT CAGAGACACC    240

CAGTGGCCCA GGTGGGCGTG GGGCCAGGGC GCAGACGAGA AGGGGCACGA GGGCTCCGCT    300

CCGAGGACCC AGCGGCAAGC ACCGGTCCCG GGCGCGCCCC AGCCCACCCA CTCGCGTGCC    360

CACGGCGGCA TTATTCCCTA TAAGGATCTG AACGATCCGG GGGCGGCCCC GCCCCGTTAC    420

CCCTTGCCCC CGGCCCCGCC CCCTTTTTGG AGGGCCGATG AGGTAATGCG GCTCTGCCAT    480

TGGTCTGAGG GGGCGGGCCC CAACAGCCCG AGGCGGGGTC CCCGGGGGCC CAGCGCTATA    540
```